United States Patent
Bryant et al.

[19]

[11] Patent Number: 6,148,817
[45] Date of Patent: Nov. 21, 2000

[54] MULTI-PART HEADBAND AND RESPIRATOR MASK ASSEMBLY AND PROCESS FOR MAKING SAME

[75] Inventors: John W. Bryant; Desmond T. Curran, both of Durham, United Kingdom; James F. Dyrud, New Richmond, Wis.; Christopher P. Henderson, Durham, United Kingdom; Harold J. Seppala, St. Paul, Minn.; Elfed I. Williams, Llanelli, United Kingdom

[73] Assignee: 3M Innovative Properties Company, St. Paul, Minn.

[21] Appl. No.: 09/012,376

[22] Filed: Jan. 23, 1998

Related U.S. Application Data

[62] Division of application No. 08/614,785, Mar. 8, 1996, Pat. No. 5,724,677.

[51] Int. Cl.[7] .................................................. A62B 18/08
[52] U.S. Cl. ................................ 128/207.11; 128/206.19
[58] Field of Search ........................ 128/200.24, 205.27, 128/206.12, 206.19, 206.21, 206.28, 207.11, 205.25, 206.13; 425/816; 2/200.3, 206, 452, 9

[56] References Cited

U.S. PATENT DOCUMENTS

| | | | |
|---|---|---|---|
| Re. 31,285 | 6/1983 | van Turnbout et al. | 55/155 |
| 1,323,217 | 11/1919 | Darrow | 128/207.11 |
| 1,987,922 | 1/1935 | Blatt | 128/139 |
| 1,990,199 | 2/1935 | Nemzek | 128/207.11 |
| 2,012,505 | 8/1935 | Goldsmith | 128/146 |
| 2,029,947 | 2/1936 | Schmitt et al. | 128/146 |
| 2,458,580 | 1/1949 | Fisketti et al. | 128/146 |

(List continued on next page.)

FOREIGN PATENT DOCUMENTS

| | | |
|---|---|---|
| 513006 | 11/1980 | Australia . |
| 0 500 590 B1 | 7/1995 | European Pat. Off. . |
| 3800959 C1 | 12/1988 | Germany . |
| 418 144 | 2/1967 | Switzerland . |
| 2 103 491 | 2/1983 | United Kingdom . |

OTHER PUBLICATIONS

Product Literature: "Glendale Respiratory Protection," Glendale Optical Company, Inc., (Feb. 1983).
Product Literature: "Delta Disposable Respirators," Racal Health & Safety, Inc., (1993).
Van A. Wente et al., Report No. 4364 of the Naval Research Laboratories, published May 25, 1954 entitled "Manufacture of Super Fine Organic Fibers.".
Van A. Wente et al., "Superfine Thermoplastic Fibers," *Industrial Engineering Chemistry*, Vol. 48, pp. 1342–1346.
C. N. Davis, "The Separation of Airborne Dust and Particles," *Institution of Mechanical Engineers*, London, Proceedings 1B, 1952.
S. G. Danisch et al., "A quantitative Fit Test for Dust/Mist Respirators: Part II," *Appl. Occup. Environ. Hyg.*, 7(4), 1992, pp. 241–245.

*Primary Examiner*—Aaron J. Lewis
*Attorney, Agent, or Firm*—James A. Rogers

[57] ABSTRACT

A multi-part headband attachable to a face mask blank and a method of attaching the same. The multi-part headband has a unit length corresponding to the distance between the attachment locations as measured along a surface of the face mask blank or along an axis intersecting the attachment locations, to facilitate material handling and attachment using high speed manufacturing equipment. The headband material is positioned along the headband path and attached at the left and right headband attachment locations. At least one longitudinal score line is formed in the headband material extending generally along the headband path, whereby the at least one longitudinal score line defines a multi-part headband. The face mask blank may comprise a molded cup-shaped face mask, a flat folded face mask or a variety of other face mask constructions.

31 Claims, 18 Drawing Sheets

U.S. PATENT DOCUMENTS

| | | | |
|---|---|---|---|
| 2,565,124 | 8/1951 | Durborow | 128/146 |
| 2,667,869 | 2/1954 | D'Elia | 128/206.13 |
| 2,787,791 | 4/1957 | Linney et al. | 2/200.3 |
| 2,823,387 | 2/1958 | De Villers | 2/200.3 |
| 2,998,818 | 9/1961 | Tabor et al. | 128/207.11 |
| 3,082,767 | 3/1963 | Matheson | 128/207.11 |
| 3,457,564 | 7/1969 | Holloway | 2/8 |
| 3,513,841 | 5/1970 | Seeler | 128/146.7 |
| 3,599,635 | 8/1971 | Ansite | 128/146.7 |
| 3,599,636 | 8/1971 | Gutman | 128/146.7 |
| 3,752,157 | 8/1973 | Malmin | 128/146.7 |
| 3,792,702 | 2/1974 | Delest | 128/146.7 |
| 3,802,428 | 4/1974 | Sherman | 128/200.24 |
| 3,886,597 | 6/1975 | Dupre | 2/206 |
| 3,971,373 | 7/1976 | Braun | 128/146.2 |
| 4,027,340 | 6/1977 | Hadtke | 2/206 |
| 4,084,585 | 4/1978 | Venaleck | 128/206.13 |
| 4,100,324 | 7/1978 | Anderson et al. | 428/288 |
| 4,118,531 | 10/1978 | Hauser | 428/224 |
| 4,195,629 | 4/1980 | Halford | 128/206.13 |
| 4,201,205 | 5/1980 | Bartholomew | 128/205.25 |
| 4,215,682 | 8/1980 | Kubik et al. | 128/205.29 |
| 4,248,220 | 2/1981 | White | 128/206.19 |
| 4,375,718 | 3/1983 | Wadsworth et al. | 29/592 E |
| 4,397,701 | 8/1983 | Johnson et al. | 2/206 |
| 4,414,973 | 11/1983 | Matheson et al. | 128/206.15 |
| 4,429,001 | 1/1984 | Kolpin et al. | 428/283 |
| 4,437,462 | 3/1984 | Piljay et al. | 128/207 |
| 4,488,546 | 12/1984 | Bernhardt et al. | 128/201.23 |
| 4,525,407 | 6/1985 | Ness | 428/138 |
| 4,536,440 | 8/1985 | Berg | 428/284 |
| 4,588,537 | 5/1986 | Klasse et al. | 264/22 |
| 4,592,815 | 6/1986 | Nakao | 204/165 |
| 4,603,692 | 8/1986 | Montesi | 128/207.11 |
| 4,635,628 | 1/1987 | Hubbard et al. | 128/201.17 |
| 4,670,910 | 6/1987 | Rosasco | 2/200.3 |
| 4,802,473 | 2/1989 | Hubbard et al. | 128/206.19 |
| 4,807,619 | 2/1989 | Dyrud et al. | 128/206.16 |
| 4,815,456 | 3/1989 | Rubin et al. | 128/859 |
| 4,827,924 | 5/1989 | Japuntich | 428/206.12 |
| 4,848,334 | 7/1989 | Bellm | 128/207.11 |
| 4,880,682 | 11/1989 | Hazelton et al. | 428/152 |
| 4,883,547 | 11/1989 | Japuntich | 156/73.4 |
| 4,908,878 | 3/1990 | Tarragano | 2/15 |
| 4,920,580 | 5/1990 | Liff | 2/206 |
| 4,941,212 | 7/1990 | Liff | 2/206 |
| 4,941,470 | 7/1990 | Hubbard et al. | 128/206.13 |
| 4,944,312 | 7/1990 | Smith | 128/857 |
| 4,946,539 | 8/1990 | Ales et al. | 156/495 |
| 4,957,124 | 9/1990 | Mooney | 132/200 |
| 5,010,590 | 4/1991 | Haber et al. | 2/12 |
| 5,020,533 | 6/1991 | Hubbard et al. | 128/206.23 |
| 5,036,846 | 8/1991 | Aulgur et al. | 128/207.11 |
| 5,038,776 | 8/1991 | Harrison et al. | 128/207.11 |
| 5,046,200 | 9/1991 | Feder | 2/452 |
| 5,052,084 | 10/1991 | Braun | 24/163 R |
| 5,069,205 | 12/1991 | Urso | 128/201.24 |
| 5,107,547 | 4/1992 | Scheu | 2/206 |
| 5,129,103 | 7/1992 | Gruneisen | 2/12 |
| 5,151,778 | 9/1992 | Conley | 351/156 |
| 5,181,507 | 1/1993 | Michel et al. | 128/201.25 |
| 5,237,986 | 8/1993 | Seppala et al. | 128/201.23 |
| 5,265,280 | 11/1993 | Walsh | 2/206 |
| 5,322,061 | 6/1994 | Brunson | 128/206.13 |
| 5,325,892 | 7/1994 | Japuntish et al. | 137/855 |
| 5,374,458 | 12/1994 | Burgio | 428/36.1 |
| 5,401,446 | 3/1995 | Tsai et al. | 264/22 |
| 5,408,702 | 4/1995 | Chiang | 2/428 |
| 5,429,856 | 7/1995 | Krueger et al. | 604/370 |
| 5,553,608 | 9/1996 | Reese et al. | 128/206.24 |
| 5,608,917 | 3/1997 | Landis et al. | 2/9 |
| 5,878,443 | 3/1999 | Seiler | 2/452 |
| 5,903,929 | 5/1999 | Chou | 2/452 |
| 6,012,164 | 1/2000 | Deal, III | 2/9 |

MULTI-PART HEADBAND AND RESPIRATOR MASK ASSEMBLY AND PROCESS FOR MAKING SAME

This is a division of application Ser. No. 08/614,785 filed Mar. 8, 1996, now U.S. Pat. No. 5,724,677.

FIELD OF THE INVENTION

The present invention relates to a multi-part headband having a length generally corresponding to the distance between the attachment locations on a face mask blank, and a method for attaching the same. The present invention also relates to a face mask preparable according to the method of the present invention.

BACKGROUND OF THE INVENTION

Filtration respirators or face masks are used in a wide variety of applications when it is desired to protect a human's respiratory system from particles suspended in the air or from unpleasant or noxious gases. They are also frequently worn by medical care providers to prevent the spread of harmful microorganisms either to or from the user.

Respirators can be classified as disposable respirators that are discarded after use, low maintenance respirators in which the filter is replaceable, and reusable respirators in which some or all of the components are replaceable. Disposable face masks are generally of one of two types—a molded cup-shaped form or a flat-folded form. The flat-folded form has advantages in that it can be carried in a wearer's pocket until needed and re-folded flat to keep the inside clean between use.

The flat-folded respirator face masks are typically constructed from one or more fabric webs arranged to form a face mask blank. Pleats and folds are added to affix the fabric webs into a shape desirable for a face mask. Such constructions may have a stiffening element to hold the face mask away from contact with the wearer's face. Stiffening has also been provided by fusing a pleat across the width of the face mask in a laminated structure or by providing a seam across the width of the face mask.

Some flat-folded face masks include pleats which are centrally folded in the horizontal direction to form upper and lower opposed faces. The face mask has at least one horizontal pleat essentially central to the opposed faces to foreshorten the filter medium in the vertical dimension and at least one additional horizontal pleat in each of these opposed faces. The central pleat is shorter in the horizontal dimension relative to the pleats in the opposed faces that are shorter in the horizontal dimension relative to the maximum horizontal dimension of the filter medium. The central pleat together with the pleats in opposed faces forms a self-supporting pocket.

Another embodiment of a flat-folded face mask includes a pocket of flexible filtering sheet material having a generally tapering shape with an open edge at the larger end of the pocket and a closed end at the smaller end of the pocket. The closed end of the pocket formed with fold lines defines a generally quadrilateral surface comprising triangular surfaces folded to extend inwardly of the pocket. The triangular surfaces face each other and are relatively inclined to each other when in use.

A further embodiment of a flat-folded face mask has an upper part and a lower part with a generally central part therebetween. The central part of the body portion is folded backwardly about a vertical crease or fold line that substantially divides it in half. This fold or crease line, when the mask is worn, is more or less aligned with an imaginary vertical line passing through the center of the forehead, the nose and the center of the mouth. The upper part of the body portion extends upwardly at an angle from the upper edge of the central part so that its upper edge contacts the bridge of the nose and the cheekbone area of the face. The lower part of the body portion extends downwardly and in the direction of the throat from the lower edge of the center part so as to provide coverage underneath the chin of the wearer. The mask overlies, but does not directly contact, the lips and mouth of the wearer.

Molded cup-shaped face masks are made from a pocket of filtering sheet material having opposed side walls, a generally tapering shape with an open end at the larger end and a closed end at the smaller end. The edge of the pocket at the closed end is outwardly bowed, e.g. defined by intersecting straight lines and/or curved lines, and the closed end is provided with fold lines defining a surface which is folded inwardly of the closed end of the pocket to define a generally conical inwardly extending recess for rigidifying the pocket against collapse against the face of the wearer on inhalation.

Disposable face masks often rely on a fixed, elastic strap to secure the mask to the user's head. Headbands for molded cup-shaped or flat-folded face masks must be designed to provide sufficient force to hold the face mask securely in place, while generating pressure within the "comfort zone" on user's of various head or face sizes. Insufficient force can result in leakage around the perimeter of the face mask. Variations in the shape and stiffness of face masks, as well as the size and shape of users make it difficult to determine a universal strap force value. For lightweight disposable face masks, a strap force value of 100–150 grams in a range of 20% to 300% elongation appears to be adequate.

In order to provide a headband with sufficient strap force to create an adequate face mask-to-face seal, within the "comfort zone" of a largest class of users, manufacturers have generally chosen long headband segments constructed from materials with a low modulus. For example, headbands are typically 15.2–35.6 mm (6–14 inches). Common headband materials include natural rubber, polyisoprene, polyurethane and natural and synthetic elastic braids or knits. The headbands are generally longer than the distance between the headband attachment locations whether measured along an axis intersecting the headband attachment locations or as measured along a surface of the face mask blank. Headbands having a length greater than the unit length between the attachment locations of the face mask blank are difficult to assembly on high speed manufacturing equipment for a number of reasons. For example, the slack or excess headband material can interfere with the movement of the face mask blanks along the production line. Compliant elastic headband materials are difficult to handle on high-speed manufacturing equipment. The greater the speed of the manufacturing equipment, the greater the degree of difficulty in registering the headband to the correct attachment locations.

Some elastomeric materials used for headbands, such as natural rubber, are extremely sticky. These materials are frequently treated with talc or other powders to facilitate handling and to increase comfort for the user. The talc can accumulate, however, in the manufacturing equipment. Inconsistent or uneven application of the talc can create difficulties in handling the headband material. Finally, the process of using high speed manufacturing equipment can be further complicated by attaching multiple headbands, such as a head strap and a neck strap, to a single face mask blank.

SUMMARY OF THE INVENTION

The present invention relates to a multi-part headband for a face mask and a method of attaching the same. The present invention is also directed to a face mask preparable by the multi-part headband attaching process of the present invention.

The multi-part headband has a unit length corresponding to the distance between the attachment locations as measured along a surface of the face mask blank or along an axis intersecting the attachment locations to facilitate material handling and attachment using high speed manufacturing equipment. The present method is suitable for use with molded cup-shaped or flat-folded face mask blanks, surgical masks, clean room masks and a variety of other face masks.

The process for attaching a multi-part headband to a face mask includes preparing a face mask blank having left and right headband attachment locations. The face mask blank has a headband path extending between the left and right headband attachment locations. The headband material is positioned along the headband path. The headband material is attached to at least one of the left and right headband attachment locations. At least one longitudinal score line is formed in the headband material extending generally along the headband path, whereby the at least one longitudinal score line defines at least a two-part headband.

The step of forming the at least one longitudinal score line can occur either prior to, subsequent to or simultaneous with the step of attaching the headband material to at least one of the left and right attachment locations.

In one embodiment, the headband material comprises at least one continuous thermoplastic skin layer secured to the elastomeric core. The headband material has a first modulus in an unactivated state and a second, lower modulus in an activated state. The thermoplastic skin layer forms a microtextured permanently deformed skin layer when the headband material is in the activated state. In one embodiment, the elastomeric core and the at least one thermoplastic layer are in continuous contact in the activated state. The stretch activated headband material can be handled as a film using high speed manufacturing equipment and bonded to a plurality of face mask blanks as a unit length headband, especially when in the unactivated state.

The present process may include the step of stretch activating at least a portion of the headband material prior or subsequent to the step of attachment to the face mask blank. The headband material in the unactivated state is visually distinguishable from the activated state to provide an indication of tampering.

The headband path may be an axis intersecting the left and right headband attachment locations or a path that generally follows a contour of a surface of the face mask blank. In one embodiment, the headband material extends along a headband path coextensive with a surface of the face mask blank. Where the face mask blank comprises a molded cup-shaped face mask blank, the headband path may be coextensive with a front surface of a cup portion of the face mask blank. Alternatively, the headband path may extend along an axis intersecting the attachment locations proximate the cup side of a cup-shaped face mask blank.

The longitudinal score line in the headband material may be a slit. The longitudinal score line preferably terminates prior to the left and right headband attachment locations. A punch-out may be formed in each end of the longitudinal score line to minimize tearing of the headband material during separation of the head strap and neck strap.

In one embodiment, a first lateral score line is formed extending from a first end of the longitudinal score line to an edge of the headband material and a second lateral score line is formed extending from a second end of the longitudinal score line to an opposite edge of the headband material.

The process of attaching the headband material may also include separating the headband material along the at least one longitudinal score line to form a two-part headband. In another embodiment, the longitudinal score line comprises a pair of ear receiving slits formed in the headband material proximate the left and right attachment locations. Another score line is formed orthogonal to the headband path proximate a midpoint between the left and right headband attachment points to form left and right headband portions.

The face mask blank comprises a molded cup-shaped respirator mask blank, a flat-folded respirator mask blank or a variety of other face masks. The method of attaching the headband material to the face mask blank includes thermal bonding, ultrasonic welding, adhesives, pressure sensitive adhesives, glues, staples, buckles, buttons, hooks, slots and fasteners.

In one embodiment, the step of providing the face mask blank comprises bonding portions of the face mask blank to form the face mask generally simultaneously with the step of attaching the headband material.

In the embodiments where the face mask is constructed from a web material, the left and right attachment locations may be on an external surface of the face mask or interposed between two surfaces of the web. At least a portion of the web forming the face mask blank is a filter media. The process of positioning a headband material preferably comprises feeding the headband material from a continuous roll of headband material.

In one embodiment, the step of providing the face mask blank includes forming a flat central portion of sufficient width to extend across a wearer's face from about cheekbone to cheekbone over the nose area. The central portion has at least an upper edge and a lower edge. A flat upper portion is attached substantially coextensively with the upper edge of the central portion. A flat lower portion is attached substantially coextensively with the lower edge of the central portion. The flat central portion, upper portion and lower portion may be elliptical in shape. An exhalation valve may also be installed on the face mask blank.

The present invention is also directed to a face mask preparable by the process of attaching a multi-part headband discussed herein. The present process of attaching a multi-part headband is amenable to high speed production methods and may comprise additional steps as needed for attachment of nose clips, exhalation valves and other typical respirator components.

The present invention is also directed to the multi-part headband attachable to a face mask blank discussed above. The face mask blank has left and right headband attachment locations defining a headband path. The multi-part headband comprises a headband material extendable along the headband path between the left and right attachment locations. The headband material has at least one longitudinal score line extending generally along the headband path, whereby the at least one longitudinal score line defines at least a two-part headband.

In one embodiment, the headband material is a stretch activated composite in either the activated or unactivated state. The stretch activated composite when in the activated state is visually distinguishable from the unactivated state, to provide an indication of tampering.

Definitions as used in this application:

"Face mask" is used herein to describe respirators, surgical masks, clean room masks, face shields, dust masks and a variety of other face coverings.

"Headband path" is used herein to describe a path between the left and right attachment locations measured generally along a surface of the face mask blank or along an axis intersecting the left and right attachment locations.

"Stretch activated elastic" is used herein to describe a material that has a first modulus prior to stretch activation and a second, lesser modulus after being activated by stretching. Some stretch activated elastic materials also increase in length after stretch activation. The modulus is measured at the initial slope of the stress/strain curve whether measured before or after stretch activation.

"Thermal bonding" is used herein to describe bonding materials having a thermoplastic component using a hot bar, ultrasonic or impulse welding, or other thermal process sealer.

"Thermoplastic" means a polymeric material having a thermoplastic component which may include polyolefins, polyesters, polyetheresters, and polyamides. Examples of suitable thermoplastic polymers include, by way of illustration only, such polyolefins as polyethylene, polypropylene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, and the like; such polyesters as poly(ethylene terephthalate), poly(tetramethylene terephthalate), poly(cyclohexylene-1,4-dimethylene terephthalate) or poly(oxymethylene-1,4-cyclohexylenemethyleneoxyterephthaloyl), and the like; such polyetheresters as poly(oxyethylene)-poly(butylene terephthalate), poly(oxytrimethylene)-poly(butylene terephthalate), poly(oxytetramethylene)-poly(butyleneterephthalate), poly(oxytetramethylene)-poly(ethylene terephthalate), and the like; and such polyamides as poly(6-aminocaproic acid) or poly(caprolactam), poly(hexamethylene adipamide), poly(hexamethylene sebacamide), poly(11-aminoundecanoic acid), and the like.

"Unit length" is used herein to describe the distance between the left and right attachment locations as measured generally along a surface of the face mask blank or along an axis intersecting the left and right attachment locations.

DETAILED DESCRIPTION OF THE PREFERRED EMBODIMENTS

Figure 1:
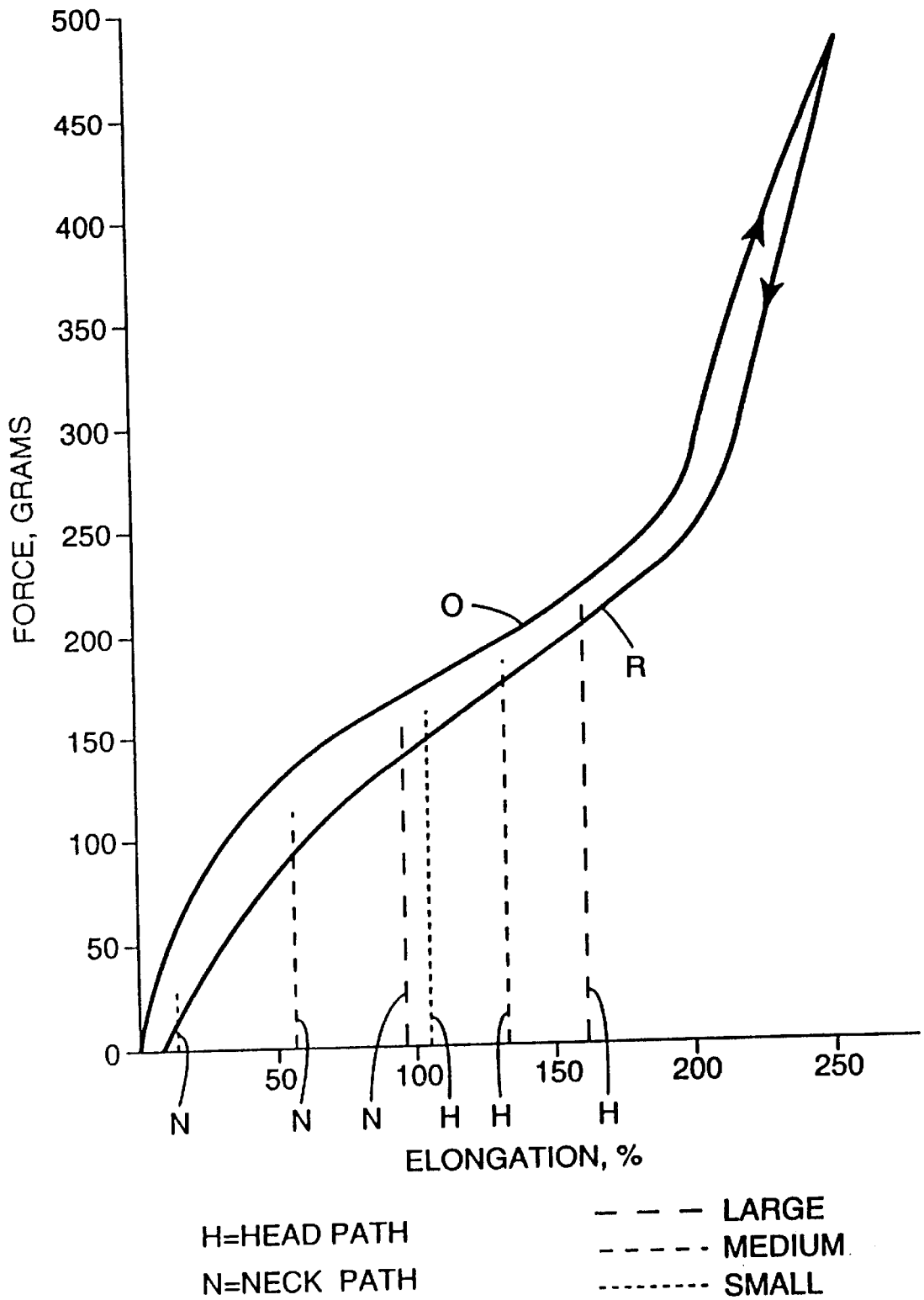
FIG. 1 is an exemplary force-elongation curve for a headband material.

The headband must hold the respirator to the wearer's face with sufficient force to prevent leakage yet it should not exert such a large force that the respirator is uncomfortable to wear. It is also desirable to provide a respirator with a headband in a single size that can be worn by all wearers in spite of differences in head size. These requirements can be met by elastomeric headbands of the present invention. Ideally, a small extension of the headband should provide a relatively large force, to accommodate the minimum force requirements for a wearer with a smaller head size, while further extension should provide an almost constant force or at least a smaller increase in force, to accommodate the wearer with a larger head size.

It has been found that for many light weight disposable respirators a minimum force of about 30 grams is required to provide a sufficiently tight fit, and a force of at least about 50 grams is preferred. In general, the greater the force, the greater will be the discomfort when the respirator is worn for a prolonged period of time. It has been found, however, that a maximum force of about 300 grams is generally satisfactory and a maximum force of about 200 grams is preferred. These forces correspond to elongation of the headband of about 15% to 120% for the preferred headband material. It is also desirable to be able to stretch the headband to about 300% or more without requiring undue force to easily place the headband over the head or head covering.

Since the length of a non-adjustable headband is fixed for a given respirator, the variables the respirator designer has to work with include the choice of the elastomeric material, its width and its thickness. For any given elongation, the force will be proportional to both the width and the thickness of the elastomeric material. Headband widths are typically in the range of about 6 mm to 10 mm. The suitability of a given headband material and thickness may be determined by the following procedure. From the force-elongation curve (or stress-strain curve) the force necessary to give an elongation to fit the minimum head size, for example 30%, is compared to the thickness of the elastomeric material at a constant width in the above range of typical widths. Thicknesses providing 30 grams of force or higher are suitable to meet the minimum force requirement and thicknesses providing 50 or more grams of force are preferred. Similarly from the force-elongation curve, the force necessary to give an elongation to fit the maximum head size, for example 160%, is compared to the thickness of the elastomer. Thicknesses providing 300 grams of force or less are suitable to meet the maximum force requirement and thicknesses providing 200 grams of force or less are preferred. Thicknesses meeting both requirements are suitable for use in this invention.

In one embodiment, the headband material is a stretch activated, elastomeric composite that has a first modulus when in the inactivated state and a second, lower modulus when in the activated state. The elastomeric composite is generally elongated 200–600% during stretch activation and allowed to recover. The stretch activated, elastomeric composite tends to permanently elongate about 25–75% after stretch activation. Additionally, stretch activation orients the molecules on the skin of the headband material to create a microstructured surface that is both visibly and tactually distinguishable from the headband material in the unactivated state. The initial higher modulus of the elastomeric composite in the unactivated or partially activated state assists in material handling during manufacturing. Normal elastics are much more sensitive to effective length variations caused by tension variations on the feeding and attaching equipment.

Stretch activated, elastomeric composites useful in the present invention may be constructed from an elastomeric core surrounded by an inelastic matrix that when stretched and allowed to recover will create an elastomeric composite, such as disclosed in U.S. Pat. No. 5,429,856 issued to Krueger et al. on Jul. 4, 1995 and U.S. Pat. No. 4,880,682 issued to Hazelton et al. on Nov. 14, 1989, both of which are hereby incorporated by reference.

An alternate elastomeric composite is disclosed in allowed U.S. patent application Ser. No. 07/503,716, filed Mar. 30, 1990, which is hereby incorporated by reference. The elastomeric composite is a non-tacky, multi-layer elastomeric laminate comprising at least one elastomeric core and at least one relatively nonelastomeric skin layer. The skin layer is stretched beyond its elastic limit and is relaxed with the core so as to form a microstructured skin layer. Microstructure means that the surface contains peak and valley irregularities or folds which are large enough to be perceived by the unaided human eye as causing increased opacity over the opacity of the composite before microstructuring, and which irregularities are small enough to be perceived as smooth or soft to human skin. Magnification of the irregularities is required to see the details of the microstructured texture. A force-elongation curve for one exemplary embodiment of an elastomeric composite in the activated state corresponding to an average of the force measured during the outgoing elongation cycle and the return cycle is illustrated in FIG. 1. The curve "O" is the force-elongation curve in the outgoing elongation direction and the curve "R" is the force-elongation curve in the return direction.

The elastomer layer can broadly include any material which is capable of being formed into a thin film layer and exhibits elastomeric properties at ambient conditions. Elastomeric means that the material will substantially resume its original shape after being stretched. Further, preferably, the elastomer will sustain only small permanent set following deformation and relaxation which set is preferably less than 20 percent and more preferably less than 10 percent at moderate elongation, e.g., about 400–500%. Generally any elastomer is acceptable which is capable of being stretched to a degree that causes relatively consistent permanent deformation in a relatively nonelastic skin layer. The elongation can be as low as 50% elongation. Preferably, however the elastomer is capable of undergoing up to 300 to 1200% elongation at room temperature, and most preferably 600 to 800% elongation at room temperature. The elastomer can be both pure elastomers and blends with an elastomeric phase or content that will still exhibit substantial elastomeric properties at room temperature.

The skin layer can be formed of any semi-crystalline or amorphous polymer that is less elastic than the core layer(s) and will undergo permanent deformation at the stretch percentage that the elastomeric composite will undergo. Therefore, slightly elastic compounds, such as some olefinic elastomers, e.g. ethylene-propylene elastomers or ethylene-propylene-diene terpolymer elastomers or ethylenic copolymers, e.g., ethylene vinyl acetate, can be used as skin layers, either alone or in blends. However, the skin layer is generally a polyolefin such as polyethylene, polypropylene, polybutylene or a polyethylene- polypropylene copolymer, but may also be wholly or partly polyamide such as nylon, polyester such as polyethylene terephthalate, polyvinylidene fluoride, polyacrylate such as poly(methyl methacrylate) and the like, and blends thereof. The skin layer material can be influenced by the type of elastomer selected. If the elastomeric core is in direct contact with the skin layer the skin layer should have sufficient adhesion to the elastomeric core layer such that it will not readily delaminate. Further where a high modulus elastomeric core is used with a softer polymer skin layer a microtextured surface may not form.

The skin layer is used in conjunction with an elastomeric core and can either be an outer layer or an inner layer (e.g., sandwiched between two elastomeric layers). Used as either an outer or inner layer the skin layer will modify the elastic properties of the elastomeric composite.

One advantage of the elastomeric composite disclosed in U.S. application Ser. No. 07/503,716 is the ability to control the shrink recovery mechanism of the composite depending on the conditions of film formation, the nature of the elastomeric core, the nature of the skin layer, the manner in which the composite is stretched and the relative thicknesses of the elastomeric and skin layer(s). By controlling these variables in accordance with the teaching of Ser. No. 07/503,716 the elastomeric composite can be designed to instantaneously recover, recover over time or recover upon heat activation.

At very thick skins, there is almost no surface microstructure produced at any stretch ratio, even with the application of heat. The elastomeric composite retains a relatively constant width after it had been restretched. This non-necking characteristic helps prevent the composite from biting into the skin of a wearer. Generally, the skin layer will hinder the elastic force of the core layer with a counteracting resisting force. The skin will not stretch with the elastomer after the composite has been activated, the skin will simply unfold into a rigid sheet. This reinforces the core, resisting or hindering the contraction of the elastomer core including its necking tendency. The microtexturing is controllable not only by the manner in which the elastomeric composite is stretched but also by the degree of stretch, the overall composite thickness, the composite layer composition and the core to skin ratio.

Figure 2:
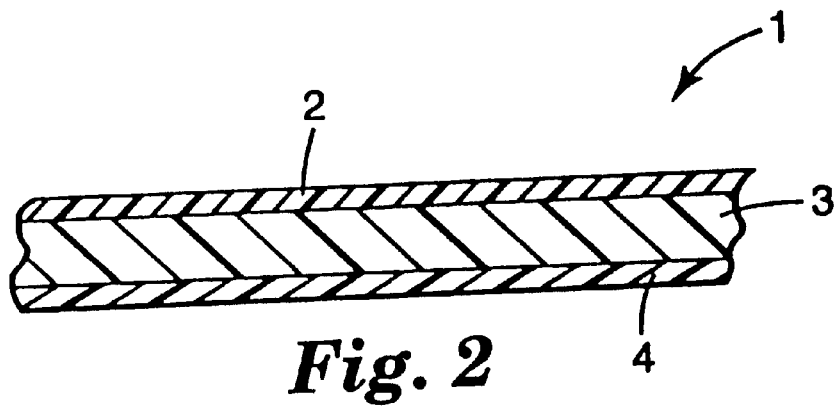
FIG. 2 is a cross-sectional segment of an elastomeric composite.

FIG. 2 shows a three layer composite construction 1 in cross section, where the core 3 is the elastomeric core secured to skin layers 2 and 4. The skins 2, 4 may be the same polymer or different polymers. This layer arrangement is preferably formed by a coextrusion process. Whether the composite is prepared by coating, lamination, sequential extrusion, coextrusion or a combination thereof, the composite formed and its layers will preferably have substantially uniform thicknesses across the composite. Preferably the layers are coextensive across the width and length of the composite. With such a construction the microtexturing is substantially uniform over the elastomeric composite surface and provides a generally uniform coefficient of friction along the surface of the composite. Composites prepared in this manner have generally uniform elastomeric properties with a minimum of edge effects such as curl, modulus change, fraying and the like.

Figure 3:
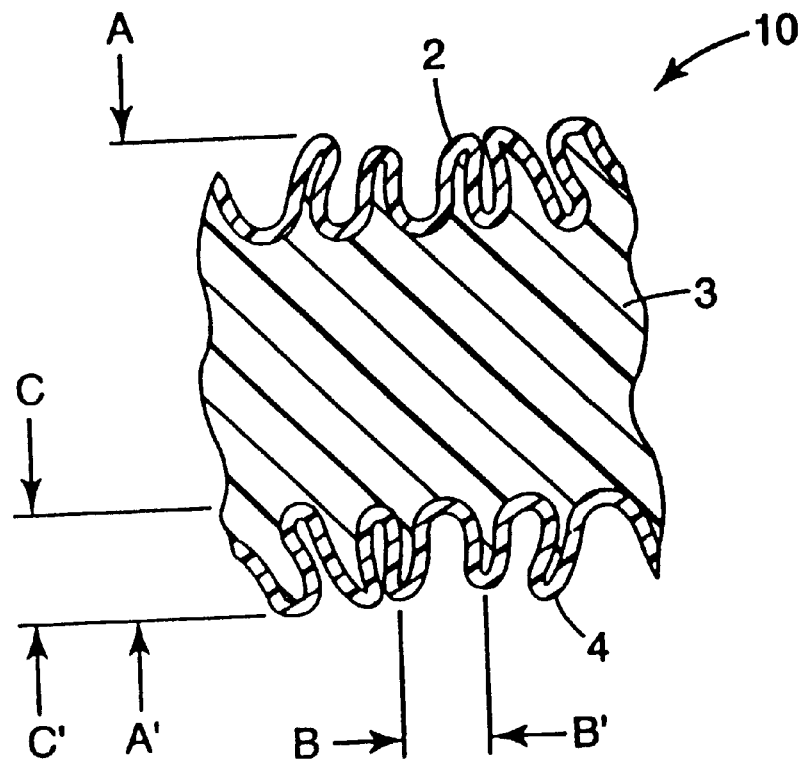
FIG. 3 is a cross-sectional segment of FIG. 2 of the composite with microstructuring caused by uniaxial stretching.

FIG. 3 is a schematic diagram of the common dimensions which are variable for uniaxially stretched and recovered composites. The general texture is a series of regular repeating folds. These variables are the total height A-A', the peak to peak distance B-B' and the peak to valley distance C-C'. A further feature of the composite depicted in FIG. 3 is that when the material is stretched and recovered uniaxially, regular, periodic folds are generally formed. That is for any given transverse section the distance between adjacent peaks or adjacent valleys is relatively constant.

FIG. 3 illustrates a microstructured surface that has been stretched past the elastic limit of the outer skin layers 2, 4 in the longitudinal direction and allowed to recover to form a microstructured surface. The microstructured surface consists of relatively systematic irregularities whether stretched uniaxially or biaxially. These irregularities increase the opacity of the surface layers of the composite, but generally do not result in cracks or openings in the surface layer when the layer is examined under a scanning electron microscope. Microtexturing also affects the properties of the formed film. Uniaxially stretching will activate the film to be elastic in the direction of stretch. Biaxially stretching will create unique surfaces while creating a composite which will stretch in a multitude of directions and retain its soft feel, making the so stretched composite particularly well suited for headband use. It has also been found that the fold period of the microstructured surface is dependent on the core/skin ratio. It is also possible to have more than one elastomeric core member with suitable skins and/or tie layer(s) in between. Such multilayer embodiments can be used to alter the elastomeric and surface characteristics of the composite.

It has also been found that the manner in which the film is stretched effects a marked difference in the texture of the microstructured surface. For example, the extruded multilayer film can be stretched uniaxially, sequentially biaxially, or simultaneously biaxially, with each method giving a unique surface texture and distinct elastomeric properties. When the film is stretched uniaxially, the folds are microscopically fine ridges, with the ridges oriented transversely to the stretch direction. When the composite is stretched first in one direction and then in a cross direction, the folds formed on the first stretch become buckled folds and can appear worm-like in character, with interspersed cross folds. Other textures are also possible to provide various folded or wrinkled variations of the basic regular fold. When the film is stretched in both directions at the same time the texture appears as folds with length directions that are random. Using any of the above methods of stretching, the surface structure is also dependent, as stated before, upon the materials used, the thickness of the layers, the ratio of the layer thicknesses and the stretch ratio.

The continuous microstructured surfaces of the invention can be altered and controlled by the proper choice of materials and processing parameters. Differences in the material properties of the layers can change the resulting microtextured skin, but it has been found that by the careful choice of the layer ratios, total composite film thickness, the number of layers, stretch degree, and stretch direction(s) it is possible to exercise significant control over the microstructure of the surface of the composite.

The degree of microtexturing of elastomeric composites prepared in accordance with the invention can also be described in terms of increase in skin surface area. Where the composite shows heavy textures the surface area will increase significantly. As the stretch ratio increases so does the percent increase in surface area, from the unstretched to the stretched and recovered composite. The increase in surface area directly contributes to the overall texture and feel of the composite surface.

The counter balancing of the elastic modulus of the elastomeric core and the deformation resistance of the skin layer also modifies the stress-strain characteristics of the composite. This also can be modified to provide greater wearer comfort when the composite is used in a headband. This relatively constant stress-strain curve can also be designed to exhibit a sharp increase in modulus at a predetermined stretch percent, i.e., the point at which the skin was permanently deformed when activated. The non-activated or non-stretched composite, as such is easier to handle for high speed attachment to a face mask than would be a conventional elastic.

In an embodiment where the stretch activated, elastomeric composite is utilized as a headband for a face mask, it may be attached to the mask in an unactivated, partially activated or a completely activated state. In the unactivated state, the headband material is not yet elastomeric and moderate processing tension such as unwinding a roll will not cause it to stretch. The elastomeric composites are advantageously handled by high speed processing equipment when in the unactivated state. The activation by stretching the headband may be performed at the factory after attachment, or it may be performed by the customer. If it is performed by the customer, the unactivated headband is visually and tactually distinguishable from an activated headband so that it can provide an indication of tampering.

The thermoplastic skin layer of the composite structures of the present headband has a particularly smooth feel on the skin and hair of the wearer. These features are in contrast to a headband made of most elastomeric materials, which often pinch and pull hair and feel coarse and rough on the skin. Activation of the materials of this invention causes this thermoplastic skin layer to become microstructured, which further enhances the beneficial feel and comfort of these materials on the skin and hair.

Alternate elastomeric materials include resilient polyurethane, polyisoprene, butylene-styrene copolymers such as, for example, KRATON™ thermoplastic elastomers available from Shell Chemical Co., but also may be constructed from elastic rubber, or a covered stretch yarn such as spandex available from DuPont Co. The alternative band designs also can include open-loop or closed loop constructions to encircle the head of the wearer, such as is disclosed in U.S. Pat. No. 5,237,986 (Seppala et al.), which is hereby incorporated by references.

FIGS. 4A–4D is a schematic illustration of an exemplary process 20 for manufacturing a flat-folded respirator that can be used with the present method of attaching a one-part or multi-part headband. A foam portion 22 is optionally positioned between an inner cover web 24 and a filter media 26. In an alternate embodiment, the foam portion 22 and/or nose clip 30 may be positioned on an outer surface of either the inner cover web 24 or outer cover web 32. A reinforcing material 28 is optionally positioned proximate center on the filter media 26. A nose clip 30 is optionally positioned along one edge of the filter media 26 proximate the reinforcing material 28 at a nose clip application station 30a. The filter media 26, reinforcing material 28 and nose clip 30 are covered by an outer cover web 32 to form a web assembly 34 shown in cutaway (see FIG. 4B). The web assembly 34 may be held together by surface forces, electrostatic forces, thermal bonding, or an adhesive.

An exhalation valve 36 is optionally inserted into the web assembly 34 at a valving station 36a. The valving station 36a preferably forms a hole proximate the center of the web assembly 34. The edges of the hole may be sealed to minimize excess web material. The valve 36 may be retained in the hole by welding, adhesive, pressure fit, clamping, snap assemblies or some other suitable means. Exemplary face masks with exhalation valves are illustrated in FIGS. 12–15, 20, and 21.

Figure 4A:
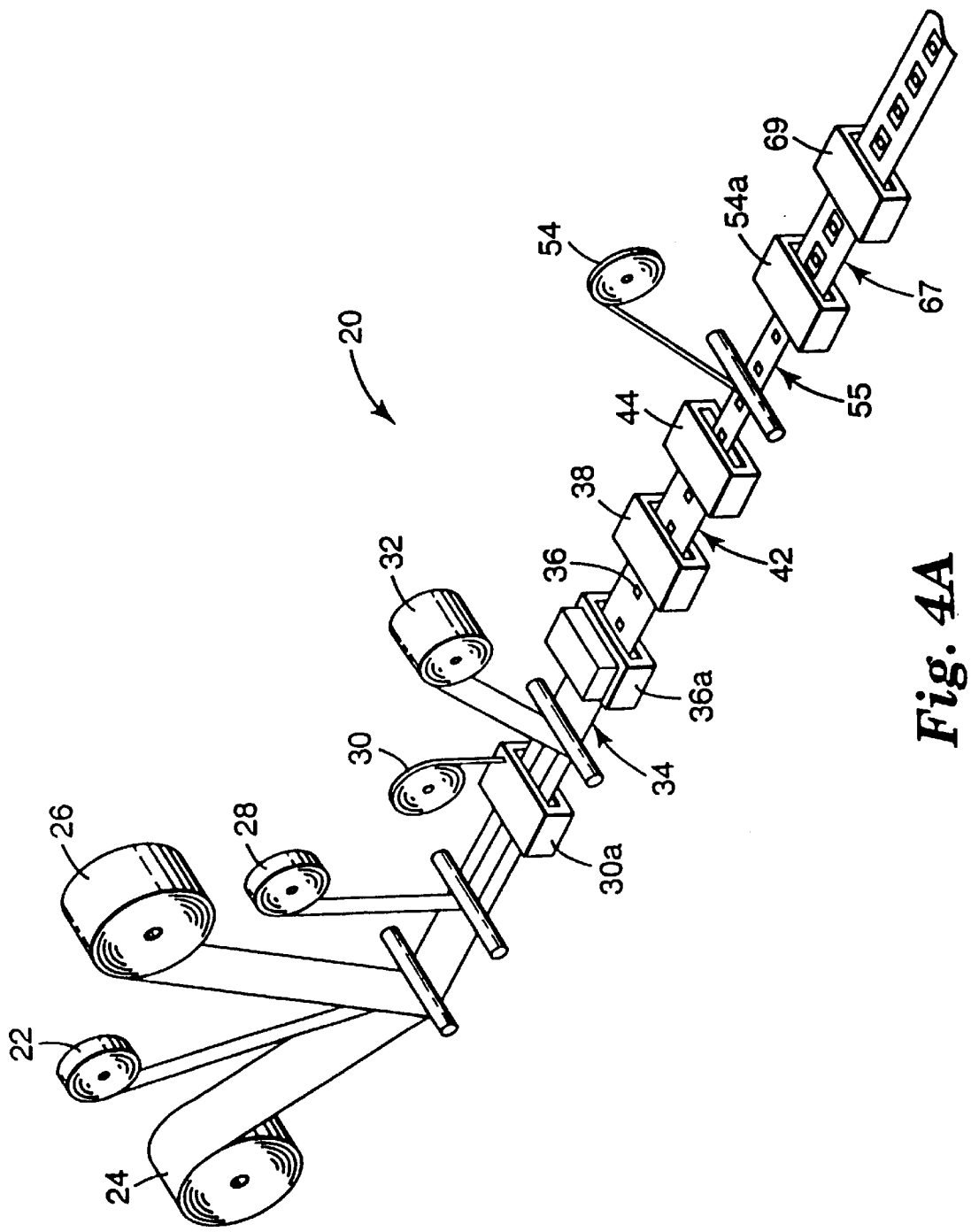
FIG. 4A is a schematic illustration of an exemplary manufacturing process for attaching a multi-part headband to a flat-folded respirator.
Figure 4B:
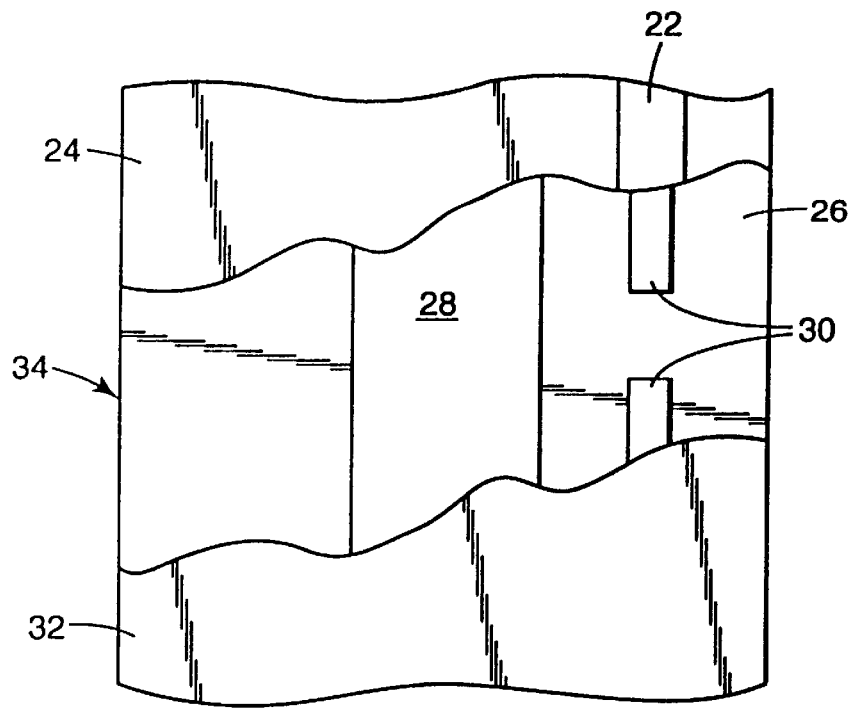
FIGS. 4B–4D illustrate intermediate web configurations of the exemplary manufacturing process of FIG. 4A.
Figure 4C:
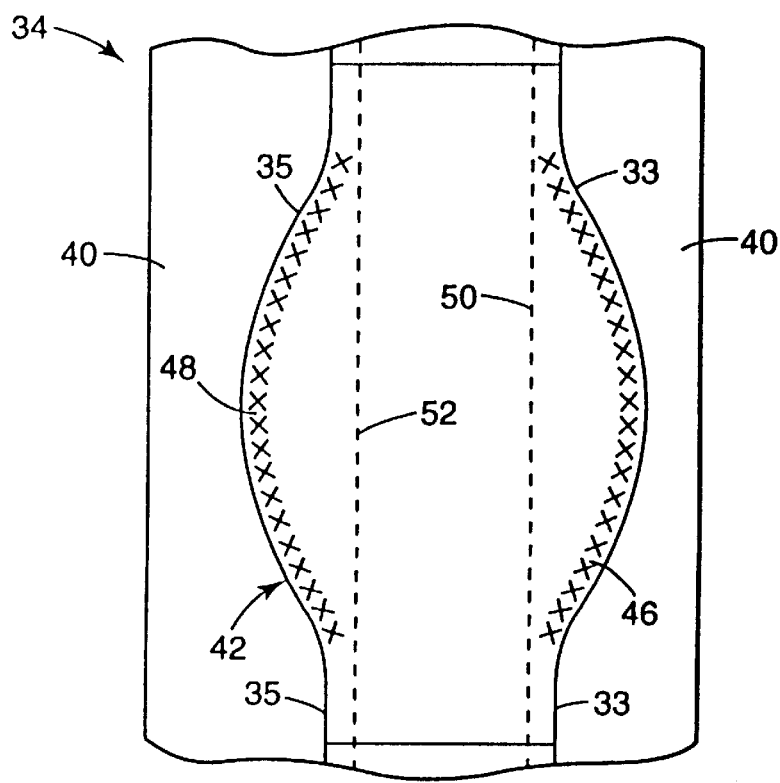
Figure 4D:
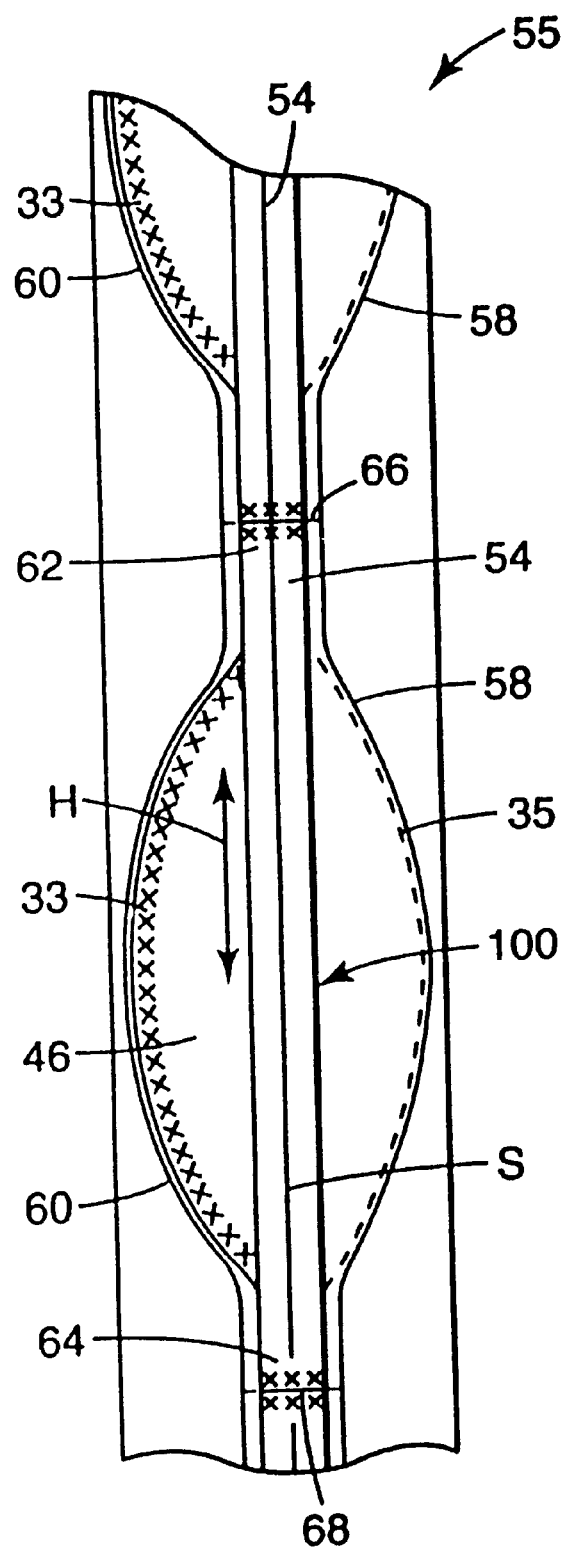

As is illustrated in FIG. 4C, the web assembly 34 is welded and trimmed along face-fit weld and edge finishing lines 33, 35 at face fit station 38. The excess web material 40 is removed and the trimmed web assembly 42 is advanced to the folding station 44. The folding station 44 folds upper and lower portions 46, 48 inward toward the center of the trimmed web assembly 42 along fold lines 50, 52, respectively, to form a folded face mask blank 55 illustrated in FIG. 4D.

The folded face mask blank 55 is welded along edges to form weld lines 58, 60 at finishing and headband attaching station 54a, forming a face mask blank 56 from which the excess material beyond the band lines can be removed. The weld line 60 is adjacent to the face-fit weld and edge finishing lines 33. The face-fit weld and edge finishing line 35 is shown in dashed lines since it is beneath the upper portion 46. Headband material 54 forming a headband 100 is positioned on the folded face mask blank 55 along a headband path "H" extending between left and right headband attachment locations 62, 64. The headband 100 is attached to the face mask blank 55 at left and right headband attachment locations 62, 64. Since the face mask blank 55 is substantially flat during the manufacturing process 20, the headband path "H" is an axis substantially intersecting the left and right attachment locations 62, 64.

It will be understood that it is possible to activate or partially activate the headband material 54 before, during or after application to the face mask blank 55. One preferred method is to activate the headband material 54 just prior to application by selectively clamping the yet unactivated headband material between adjacent clamps, elongating it the desired amount, laying the activated headband material 54 onto the face mask blank 55, and attaching the inactivated end portions of the headband material 54 to the blank 55. Alternatively, the unactivated headband material 54 can be laid onto the face mask blank 55, attached at the ends as discussed herein and then activated prior to packaging. Finally, the headband material 54 can remain unactivated until activated by the user.

A longitudinal score line "S" may optionally be formed either before, during or after attachment of the headband material 54 to the face mask blank 55 at the finishing and headband attaching station 54a to create a multi-part headband. The edges 66, 68 of the face mask blank 55 adjacent to the left and right headband attachment locations 62, 64 may either be severed to form discrete face masks or perforated to form a strip of face masks 67 (see FIG. 5A). The face masks 67 are packaged at packaging station 69. Alternate constructions for a flat-folded face mask blank are disclosed in U.S. patent application Ser. No. 08/507,449 filed Sep. 11, 1995, entitled FLAT-FOLDED RESPIRATOR AND PROCESS FOR MAKING THE SAME, which is hereby incorporated by reference.

Figure 5A:
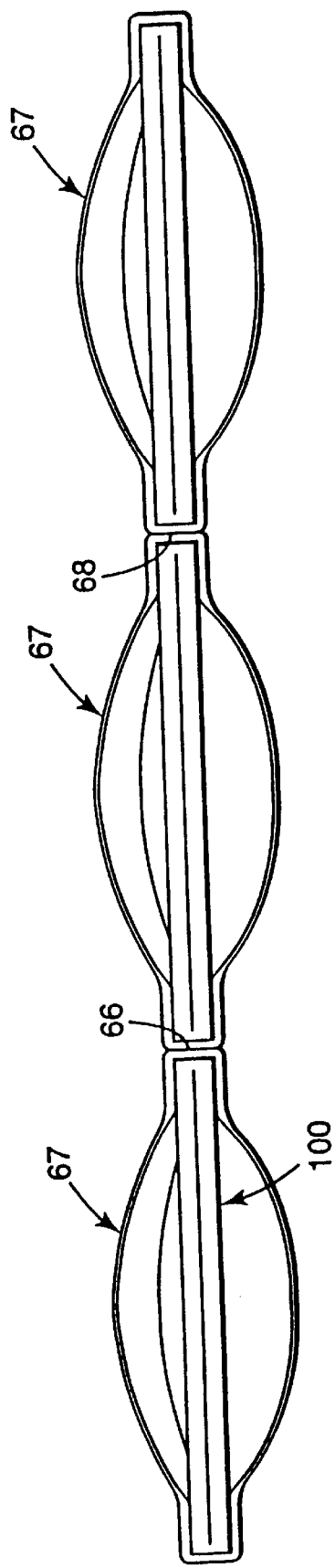
FIG. 5A illustrates a strip of face masks with a two-part, unit length headband.

FIG. 5A illustrates a strip of flat-folded face masks 67 manufactured according to the process of FIGS. 4A–4D. The edges 66, 68 are preferably perforated so that the face masks 67 can be packaged in a roll. A portion of the headband 100 at the edges 66, 68 has been removed by the perforation process. In an alternate embodiment, the headband 100 extends continuously past the edges 66, 68. FIG. 5A illustrates the multi-part headband 100 attached to the rear of the face mask 67, although it could be attached in any of the configurations disclosed herein. It will be understood that either a one-part or a multi-part headband 100 may be attached to either side of the face mask 67, in either a peel or shear configuration, although sheer is preferred.

Figure 5B:
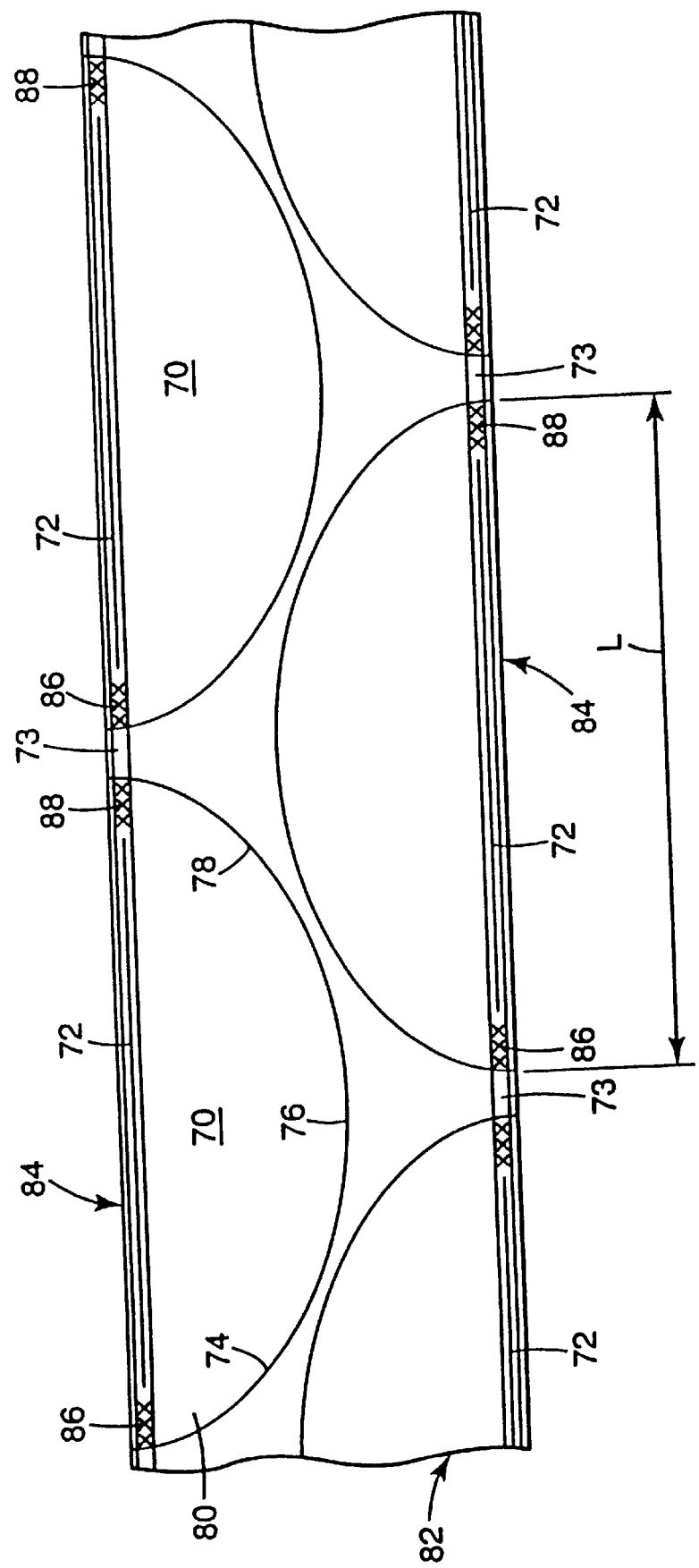
FIG. 5B is top view of a fabric web containing a plurality of exemplary face masks with a two-part unit length headband.

FIG. 5B illustrates a method of manufacturing a plurality of exemplary face masks blanks 70 with unit length, two-part headbands 72. Three sides 74, 76, 78 of top web 80 and bottom web 82 are connected to each other by heat sealing or ultrasonic bonding to form the face mask blanks 70 having a generally oval shape with an open side 84. Headband material 72 is positioned along the open sides 84, generally coplanar with the face mask blanks 70 along headband path "H" and bonded at left and right attachment locations 86, 88. The sections of headband material 72 attached to each face mask blank 70 have a unit length "L" corresponding to the distance between the left and right attachment locations 86, 88. Consequently, there is no slack in the headband material 72 during manufacturing. The unused portion of the headband material 73 between each face mask blank 70 are discarded along with the unused portions of the top and bottom webs 80, 82. In an alternate embodiment, the headband material 72 may be positioned between the top and bottom webs 80, 82. It will be understood that a one-part may be substituted for the two-part headband 72.

The headbands in any of the embodiments disclosed herein may be attached to the face masks by any suitable technique, including thermal bonding, ultrasonic welding, glues, adhesives, hot-melt adhesives, pressure sensitive adhesives, staples, mechanical fasteners such as buckles, buttons and hooks, mating surface fasteners, or openings, such as loops or slots, formed at the left or right attachment locations for entrapping the headband material. It may be attached so that the forces acting between the headband and mask when being worn by a user are in a peel mode or in a sheer mode. The headband may be attached to the mask between layers of the mask construction or on either outside surface of the mask.

FIGS. 6A–6J illustrate various alternate embodiments of a multi-part headband 100a–100j. The multi-part headband configurations are generally more conducive to high speed material handling and manufacturing equipment than multiple independent headbands. It will be understood that any of the following headband configurations may be constructed with an elastomeric composite.

Figure 6A:
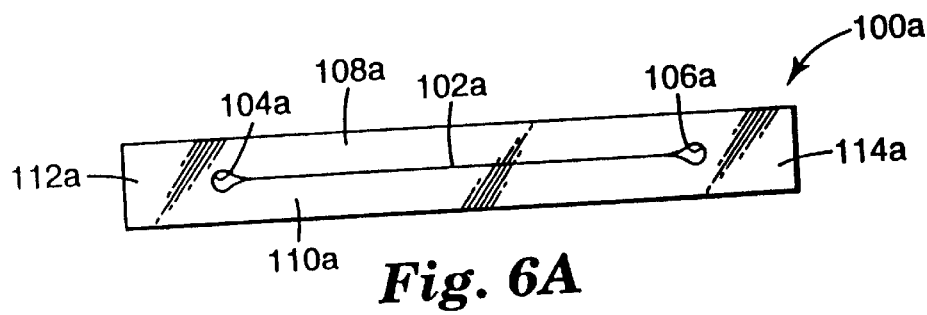
FIGS. 6A–6J illustrate alternate exemplary headband configurations.

FIG. 6A illustrates an exemplary two-part headband 100a with a longitudinal score line 102a extending between a pair of circular punch-outs 104a, 106a. The score line 102a defines a head strap 108a and a neck strap 110a of the two-part headband 100a. The punch-outs 104a, 106a minimize tearing between the head strap 102a and neck strap 104a during use. Left and right tab 112a, 114a are provided for attachment to a face mask blank (see for example, FIGS. 7–23) at the left and right attachment locations, respectively.

Figure 6B:
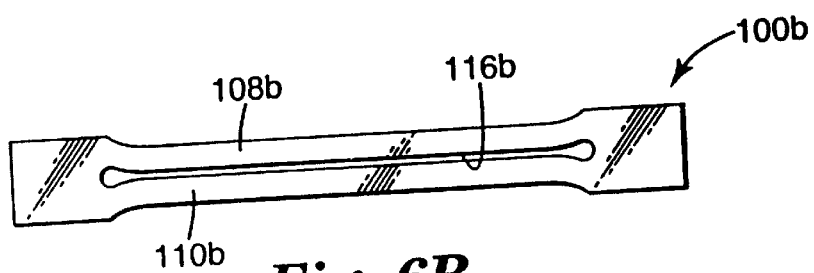

FIG. 6B illustrates the two-part headband 100b generally shown FIG. 6A constructed from a stretch activated elastic after head straps 108b and neck straps 110b have been stretch-activated. The stretch activated portion 108b and 110b becomes narrower than prior to stretch activation, shown in the inactivated left and right tabs 112b and 114b (see also FIG. 6A). The portions 108b and 110b also elongate after stretch activation, generally in the range of 125–175% of their original length. The narrowing and lengthening of the head strap 108b and neck strap 110b cause a gap 116b to form along the score line 102b. The gap 116b facilitates separating the band and the application of the headband 100b to the user's head.

Figure 6C:
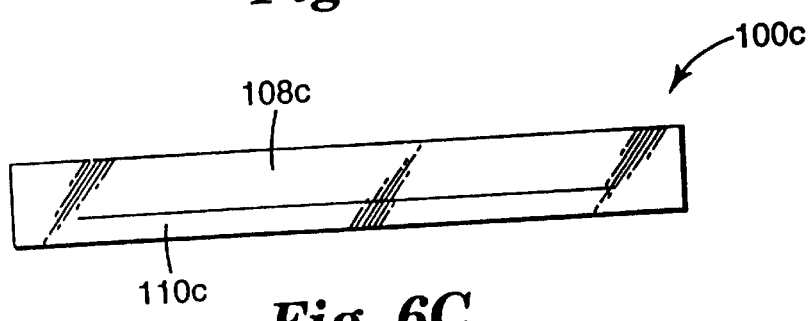

FIG. 6C illustrates an alternate embodiment of a two-part headband 110c in which the longitudinal score line 102c is off-center. Consequently, the elastic force generated by the narrower head strap 110c is less than the elastic force generated by the wider neck strap 108c, for the same elongation. For example, the straps 108c, 110c can be configured to generate the same force for different amounts of elongation.

Figure 6D:
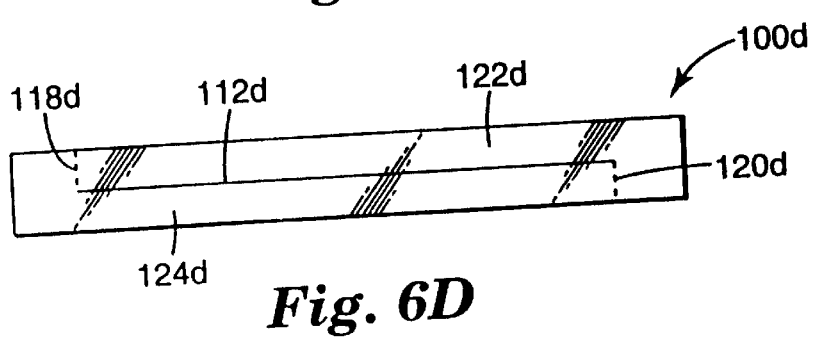

FIG. 6D illustrates an alternate embodiment of the present two-part headband 110d in which a pair of opposing score lines 118d and 120d are formed at opposite ends of the longitudinal score line 102d. The operator breaks the two-part headband 100d along the score lines 118d, 120d to form a pair of straps 122d, 124d that can be tied behind the user's head. The operator has the option to activate the stretch activated elastic of the two-part headband 100d so that the straps 122d, 124d generate an elastic force. Since the straps 122d and 124d are tied to form a single strap, a second headband 100d is required if the face mask requires both a head strap and a neck strap. Additionally, due to the overall length required to form a head strap, the elastomeric composite is particularly suited for the headband 100d.

Figure 6E:
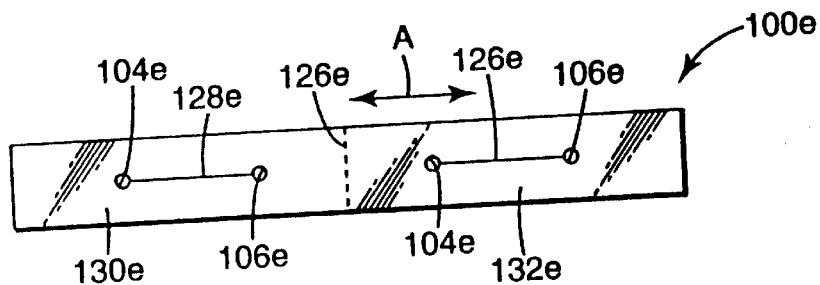

FIG. 6E illustrates an alternate two-part headband 100e in which a center score line 126e is formed orthogonal to ear receiving score lines 126e, 128e. The left and right ear receiving score lines 126e, 128e are formed in left and right ear tabs 130e, 132e. Punch-outs 104e, 106e are provided to minimize tearing of the ear tabs 130e, 132e. The user separates the two-part headband 100e into two pieces and extends the left and right ear tabs 130e, 132e around her left and right ears, respectively.

Figure 6F:
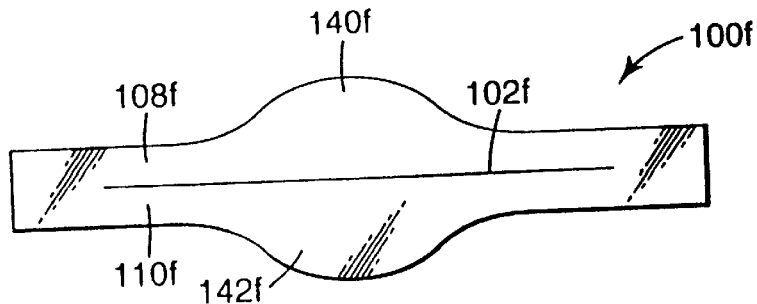

FIG. 6F illustrates an alternate two-part headband 100f with a pair of user gripping surfaces 140f, 142f on opposite sides of longitudinal score line 102f provided to facilitate separation of the head strap 108f from the neck strap 110f. The user gripping surfaces 140f, 142f also assist the user in positioning the head strap 108f and neck strap 110f on her head.

Figure 6G:
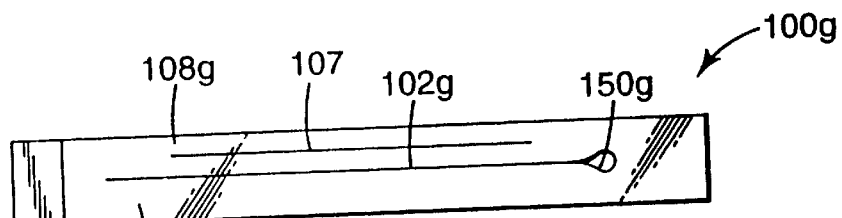

FIG. 6G illustrates an embodiment of the two-part headband 100g with a button hole 150g for engagement with a button on a face mask (not shown). In an alternate embodiment, a plurality of holes 150g are provided for adjusting the tension on the headband 100g. The longitudinal score line 102g is provided to form the head and neck straps 108g, 110g of the two-part headband as discussed above. The head strap 108g may optionally include a score line 107 to produce a head cradle. The head cradle also provides a means of adjusting the tension on the head strap 108g. The further the head cradle is opened out in the head strap 108g, the greater the tension produced.

Figure 6H:
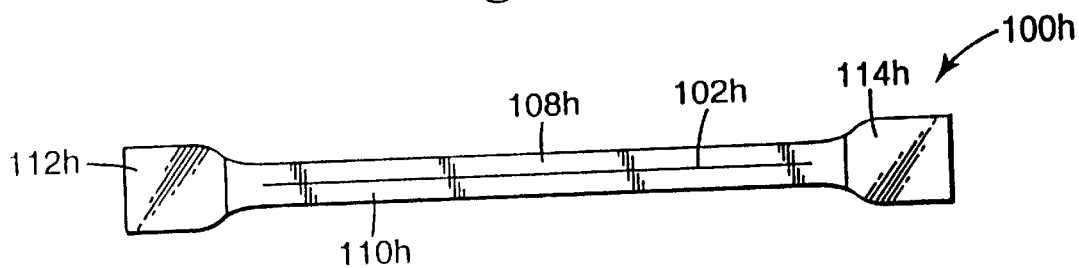

FIG. 6H illustrates a two-part headband 100h constructed of a stretch activated elastic in the activated configuration. The head and neck straps 108h, 110h are elongated and narrowed due to stretch activation. In the embodiment illustrated in FIG. 6h, left and right attachment tabs 112h and 114h have not been activated. The longitudinal score line 102h has been formed after the two-part headband 100h has been activated.

Figure 6I:
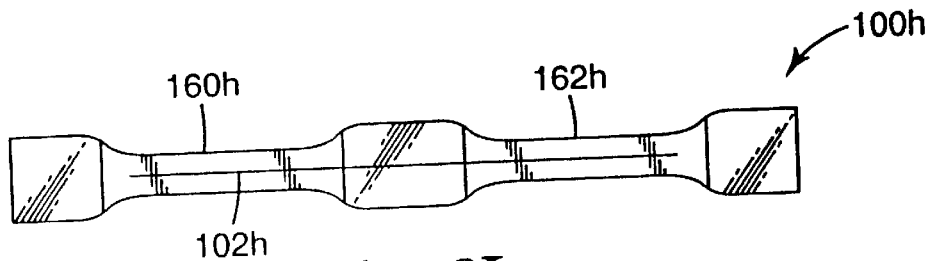

FIG. 6I illustrates a two-part headband 100i with the stretch activated elastic partially activated along two portions 160i, 162i. Partial activation allows the two-part headband 100i to accommodate a user with a smaller head size. It will be understood that a variety of activation patterns are possible and that FIG. 6i is presented for illustration only. The longitudinal score line 102i has been formed after the two-part headband 100i has been activated.

Figure 6J:
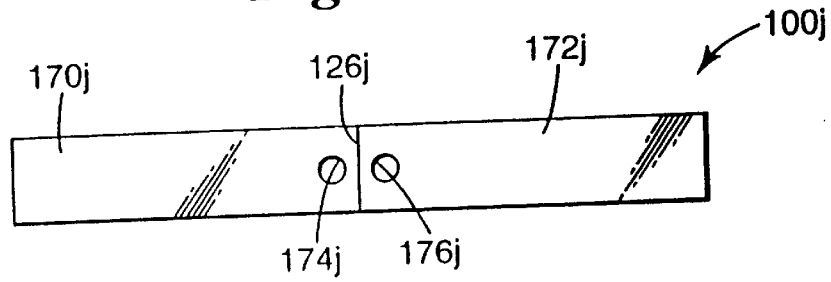

FIG. 6J illustrates a one-part headband 100j with a center score line 126j that permits left and right headband portions 170j, 172j to be joined behind the head of the user with fasteners 174j, 176j. It will be understood that a variety of fasteners may be used with the headband 100j, such as buttons, snaps and hook and loop fasteners. For example, the fastener 174j may be a button and 176j an opening for receiving the button.

Figure 7:
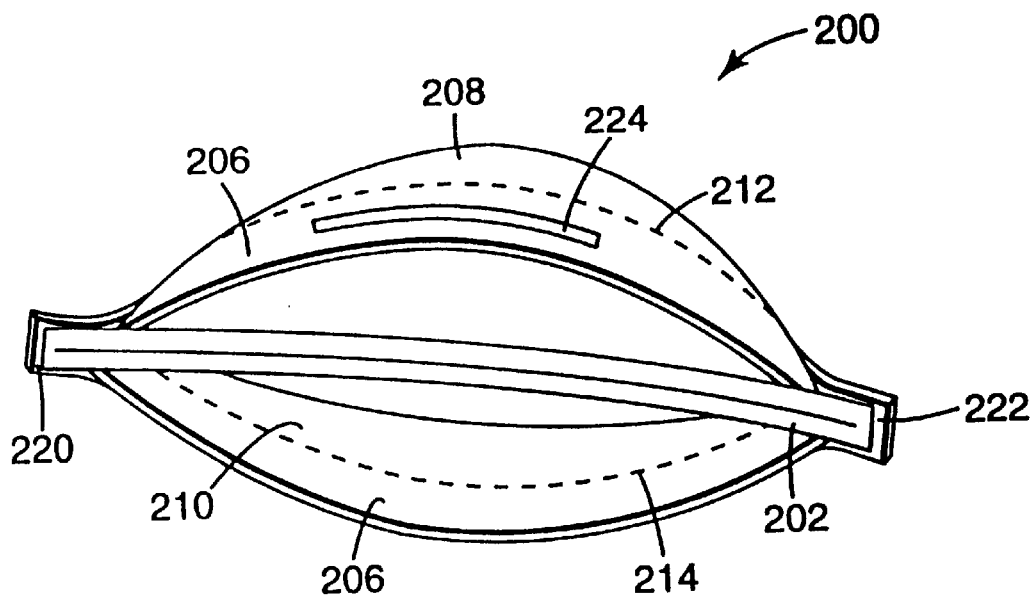
FIG. 7 is a perspective view of an exemplary flat-folded respirator shown in an open configuration.
Figure 8:
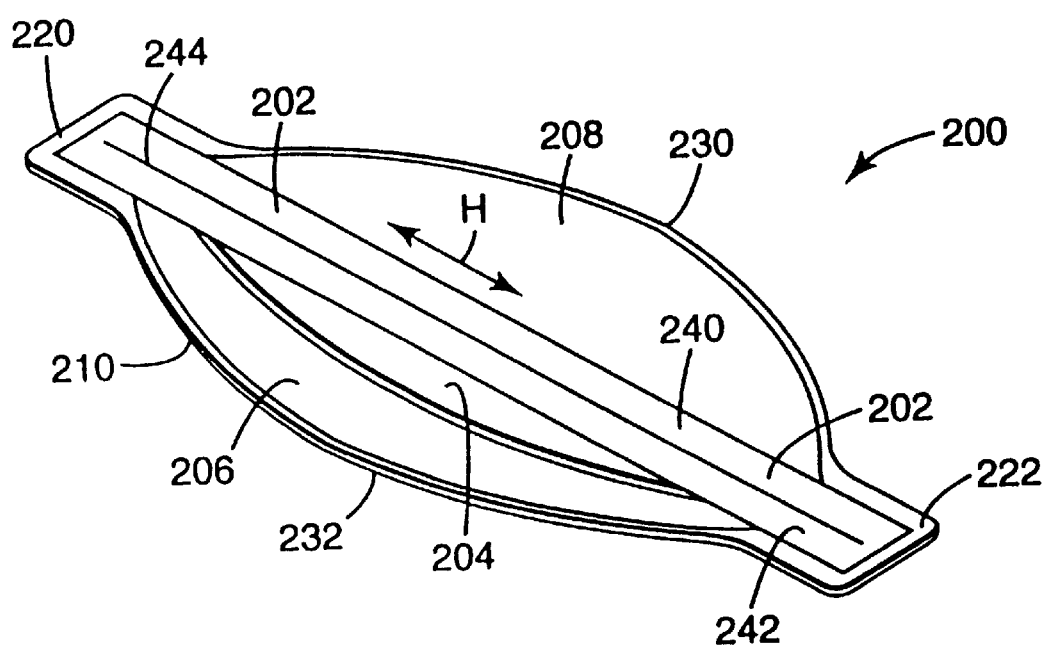
FIG. 8 is a perspective view of an exemplary flat-folded respirator shown in a folded configuration.

FIGS. 7 and 8 illustrate an elliptically shaped, flat-folded face mask 200 with a unit length, multi-part headband 202 in both an unfolded and a folded configuration, respectively. It will be understood that the shape of the flat-folded face mask 200 may vary without departing from the present invention. For example, the generally elliptical shape could be rectangular, circular, or a variety of other shapes.

As illustrated in FIG. 7, the two-part headband 202 extends along a headband path "H", generally coplanar with flat-folded face mask 200. The two-part headband 202 is attached to the face mask 200 at left and right attachment locations 220, 222 in a peel configuration. The headband 202 is divided into a head strap 240 and a neck strap 242 by score line 244. It will be understood that any of the headband configurations illustrated in FIGS. 6A–6J may be utilized with the face mask 200.

Additional portions 204 and 206 may optionally be attached to upper and lower portions 208, 210 of respirator 200 along folds 212, 214. Additional portions 204, 206 preferably are not sealed along the edges by headband attachment locations 220, 222 due to the ability of the additional portions 204 and 206 to pivot along the folds 212, 214. Optional nose clip 224 is located on additional portion 204.

The face mask 200 extends preferably about 160 to 245 mm in width between the headband attachment locations 220, 222, more preferably about 175 to 205 mm, most preferably about 185 to 190 mm in width. The height of face mask 200 extending between top edge 230 and bottom edge 232 is preferably about 30 to 110 mm in height, more preferably about 50 to 100 mm in height, most preferably about 75 to 80 mm in height. The depth of upper portion 204 extending from fold 212 to the peripheral edge of upper portion 204 is preferably about 30 to 110 mm, more preferably about 50 to 70 mm, most preferably about 55 to 65 mm. The depth of lower portion 206 extending from fold 214 to the peripheral edge of lower portion 206 is preferably about 30 to 110 mm, more preferably about 55 to 75 mm, most preferably about 60 to 70 mm. The depths of upper portion 204 and lower portion 206 may be the same or different and the sum of the depths of the upper and lower portions preferably does not exceed the height of the central portion.

Figure 9:
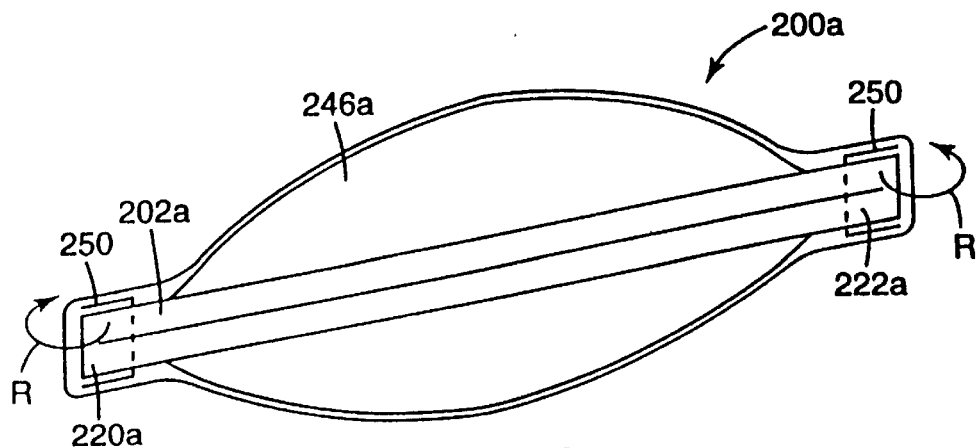
FIG. 9 is a perspective view of an exemplary flat-folded respirator with a two-part headband attached along a front surface thereof.

FIG. 9 is an alternate embodiment of a face mask 200a generally corresponding to the face mask 200 of FIGS. 7 and 8, where the two-part headband 202a is attached to a front surface 246a. To apply the mask 200a, the user wraps the two-part headband 202a around to the front (see FIGS. 7 and 8) so that the left and right attachment locations 220a, 222a are in a peel configuration. Three-sided cut-outs 250 may optionally be formed in the left and right attachment locations to convert the face mask 200a from a peel to the shear configuration. In particular, the cut-outs 250 wrap toward the rear of the face mask 200a on the path "R" along with the two-part headband 202a, providing a shear configuration. In an alternate embodiment, the cut-out 250 is a perforated cut-out that permits the user to adjust the headband tension by breaking more or less of the seal on the perforation.

Figure 10:
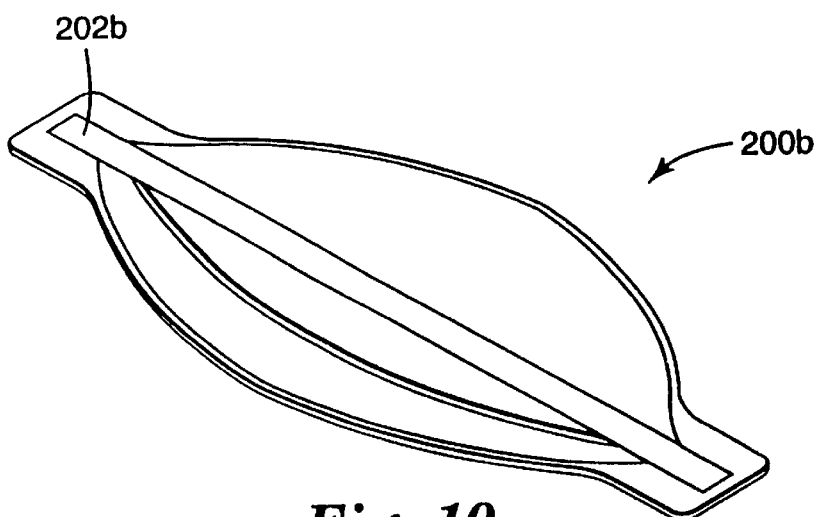
FIG. 10 is a perspective view of an exemplary flat-folded respirator with a one-part headband attached along a rear surface.
Figure 11:
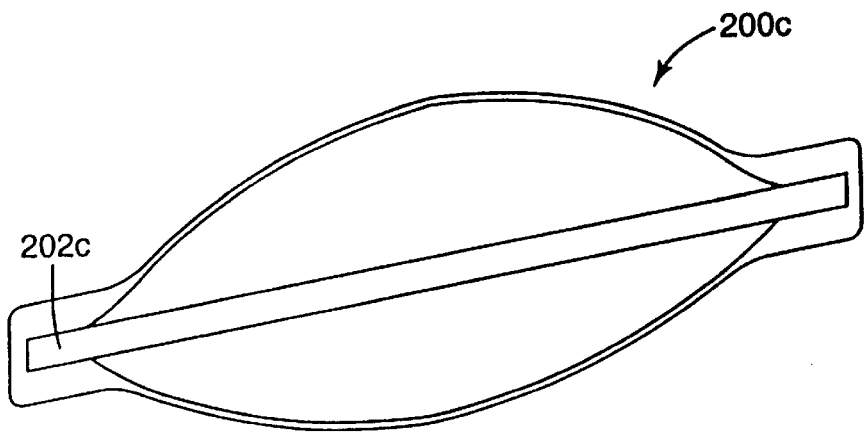
FIG. 11 is a perspective view of an exemplary flat-folded respirator with a one-part headband attached along a front surface thereof.

FIG. 10 illustrates a face mask 200b that corresponds to the face mask 200 of FIG. 8 in all respects, except that a one-part headband 202b is utilized. Likewise, FIG. 11 illustrates a face mask 200c that corresponds to the face mask 200a of FIG. 9 in all respects, except that a one-part headband 202c is utilized.

Figure 12:
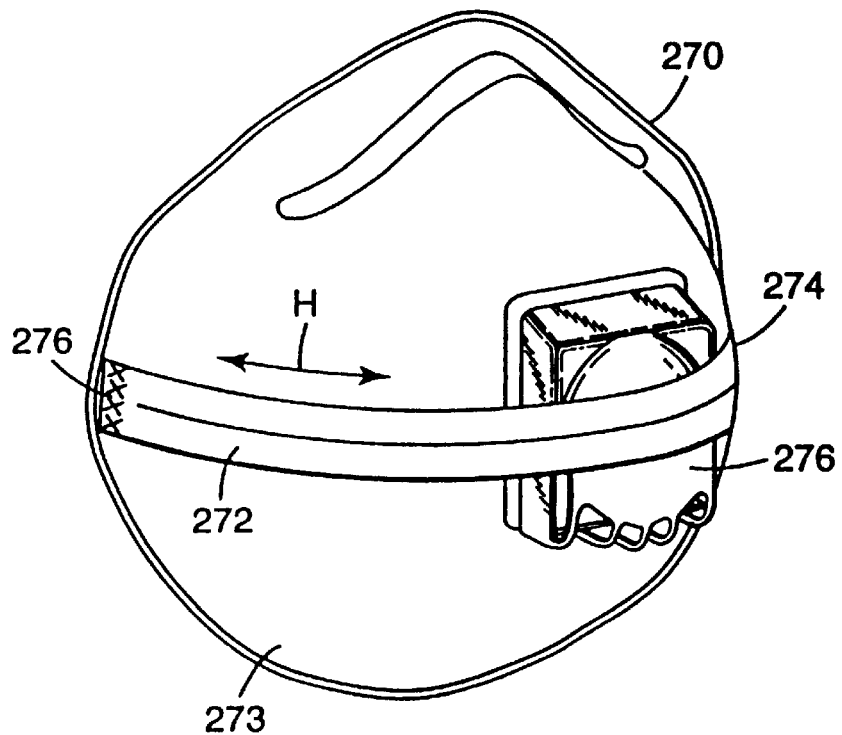
FIG. 12 illustrates a two-part headband extending along a headband path traversing an exhalation valve and the front surface of a cup-shaped face mask.

FIG. 12 illustrates a front view of a molded cup-shaped face mask 270 with a two-part headband 272 extending across a front surface 274 and an exhalation valve 276. In the embodiment illustrated in FIG. 12, the headband path "H" generally follows the contour of the front surface 273 of the face mask 270, but is not completely coextensive, especially adjacent to the exhalation valve 276. The two-part headband 272 is preferably placed in tension during manufacturing to minimize slack and the corresponding material handling difficulties encountered using high speed manufacturing equipment. The two-part headband 272 is connected to the face mask 270 at left and right attachment locations 274, 276. The user applies the face mask 270 by pulling the two-part headband 272 toward the rear of the mask 270 so that the attachment locations 274, 276 are in a peel configuration.

Figure 13:
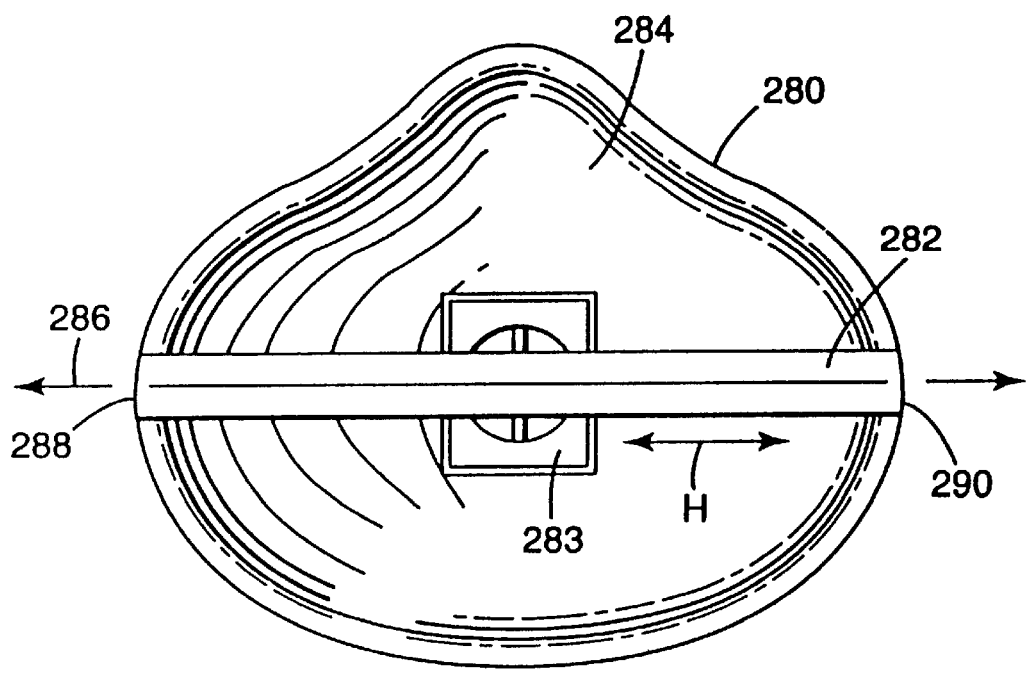
FIG. 13 illustrates a two-part headband extending along a headband path traversing the rear of a cup-shaped face mask.

FIG. 13 is a rear view of a molded cup-shaped face mask 280 with an exhalation valve 283. A unit length, two-part headband 282 extends across the rear opening 284. The headband path "H" extends along an axis 286 intersecting left and right attachment locations 288, 290.

Figure 14:
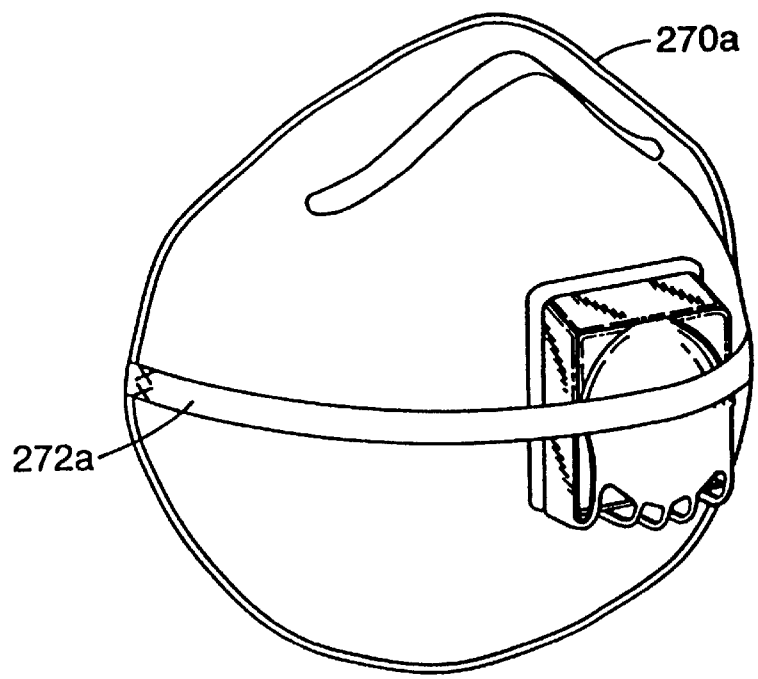
FIG. 14 illustrates a one-part headband extending along a headband path traversing an exhalation valve and the front surface of a cup-shaped face mask.
Figure 15:
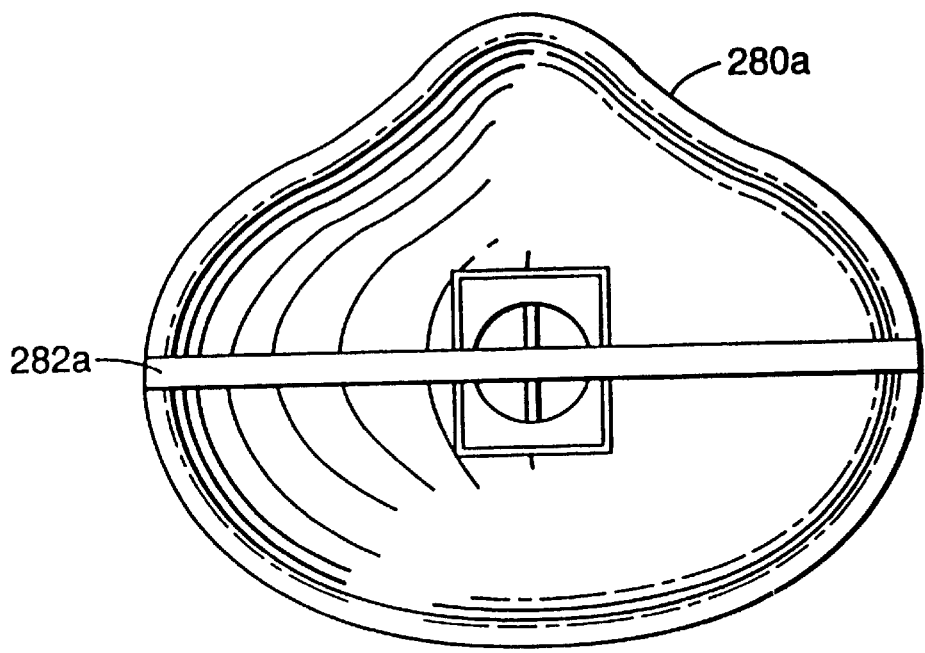
FIG. 15 illustrates a one-part headband extending along a headband path traversing the rear of a cup-shaped face mask.

FIG. 14 corresponds to the embodiment of FIG. 12 in all respects, except that a one-part headband 272a is attached to the face mask 270a. FIG. 15 corresponds to the embodiment illustrated in FIG. 13 in all respects, except that a one-part headband 282a is attached to the face mask 280a.

Figure 16:
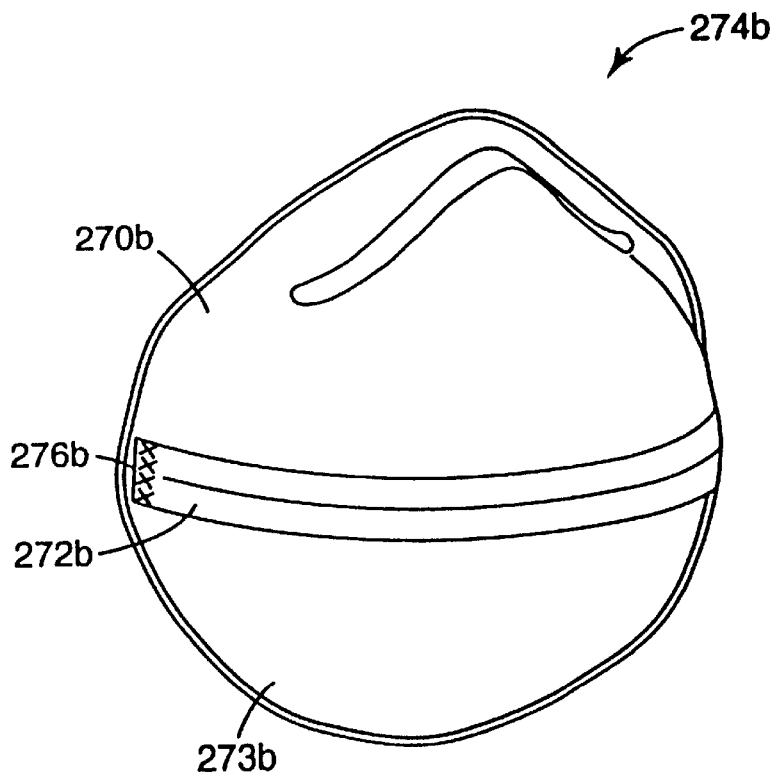
FIG. 16 illustrates a two-part headband extending along a headband path traversing the front surface of a cup-shaped face mask.

FIG. 16 illustrates a front view of a molded cup-shaped face mask 270b with a two-part headband 272b extending across a front surface 273b. Since there is no exhalation valve as is illustrated in FIG. 12, the headband 272b more closely follows the contour of the front surface 273b. The headband 272b is preferably placed in tension during manufacturing to minimize slack and the corresponding material handling difficulties encountered using high speed manufacturing equipment. The headband 272b is connected to the face mask 270b at left and right attachment locations 274b, 276b, as discussed above.

Figure 17:
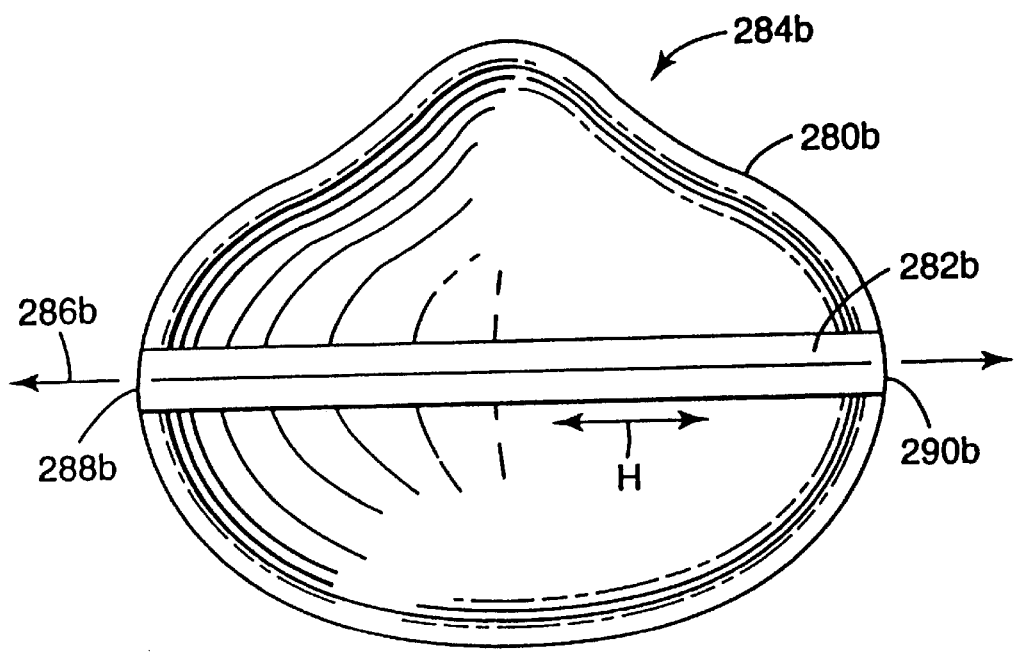
FIG. 17 illustrates a two-part headband extending along a headband path traversing the rear of a cup-shaped face mask.

FIG. 17 is a rear view of a molded cup-shaped face mask 280b with a unit length, two-part headband 282b extending across the rear opening 284b. The headband path "H" extends along an axis 286b intersecting left and right attachment locations 288b, 290b, as was discussed in connection with FIG. 13. The presence or absence of the exhalation valve 283 in FIG. 13 does not alter the headband configuration in the present embodiment.

Figure 18:
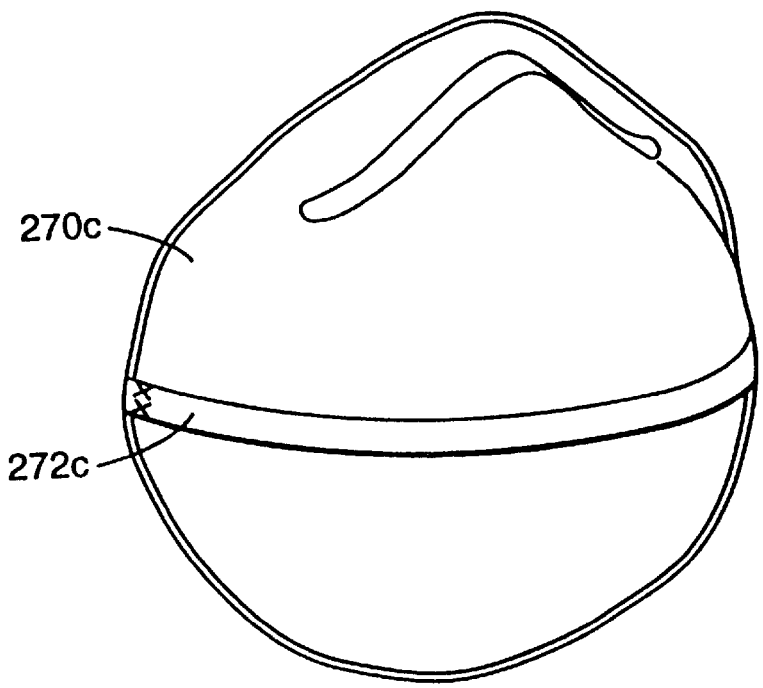
FIG. 18 illustrates a one-part headband extending along a headband path traversing the front surface of a cup-shaped face mask.
Figure 19:
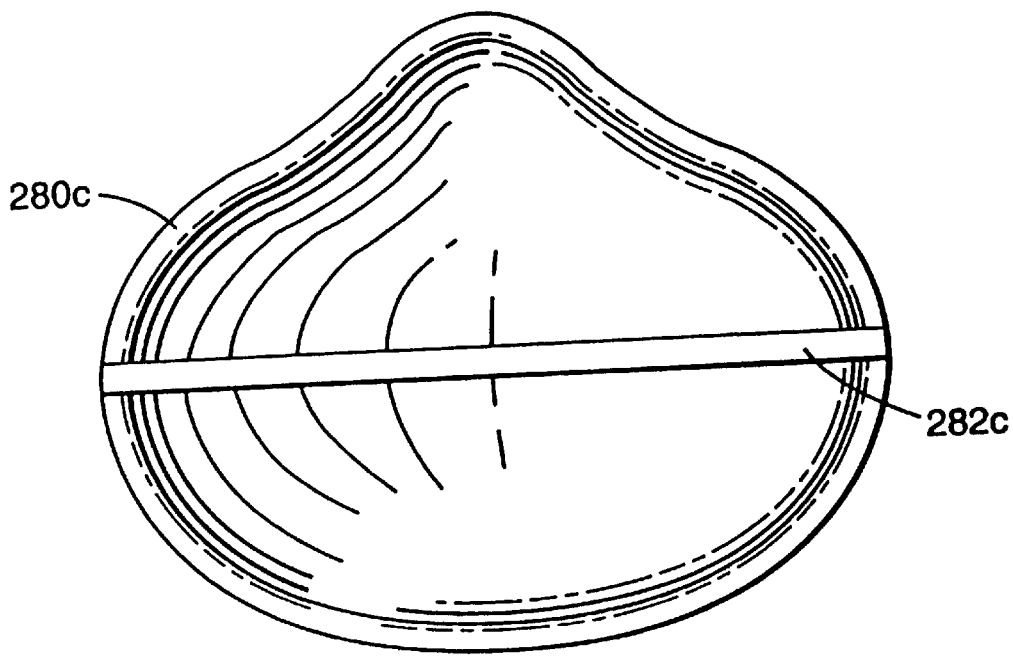
FIG. 19 illustrates a one-part headband extending along a headband path traversing the rear of a cup-shaped face mask.

FIG. 18 corresponds to the embodiment of FIG. 16 in all respects, except that a one-part headband 272c is attached to the face mask 270c. FIG. 19 corresponds to the embodiment illustrated in FIG. 17 in all respects, except that a one-part headband 282c is attached to the face mask 280c.

Figure 20:
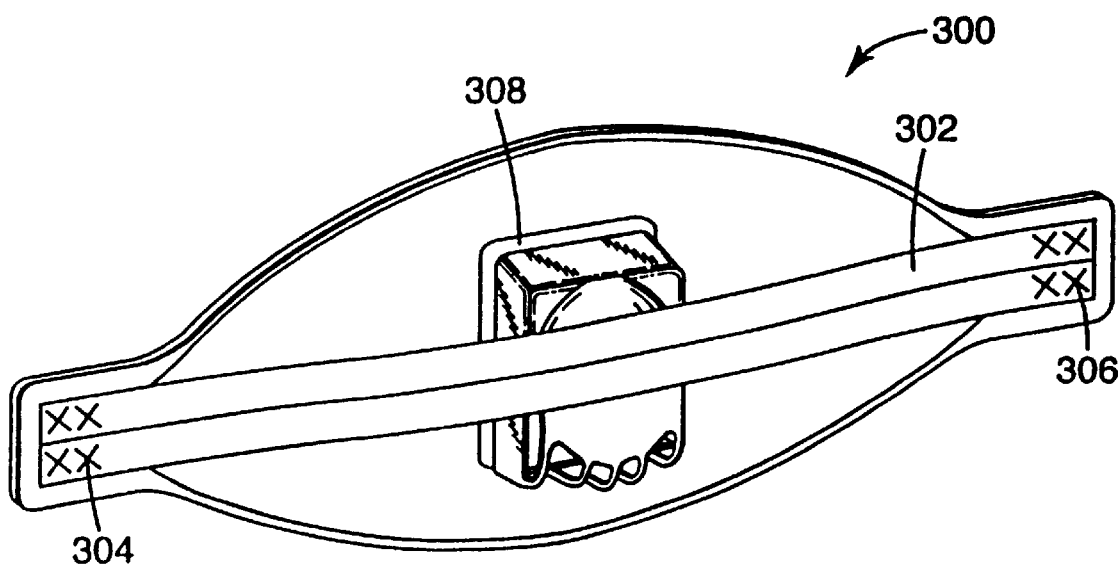
FIG. 20 illustrates a two-part headband extending along a headband path traversing an exhalation valve and the front surface of a flat folded face mask.
Figure 21:
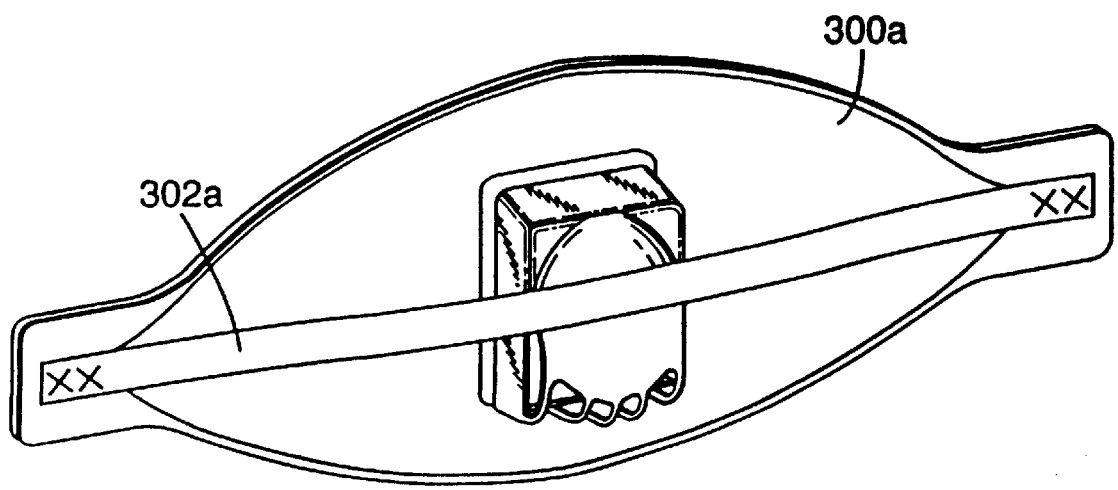
FIG. 21 illustrates a one-part headband extending along a headband path traversing an exhalation valve and the front surface of a flat folded face mask.

FIG. 20 illustrates a front view of an exemplary flat-folded face mask 300 with a two-part headband 302 attached at left and right attachment locations 304, 306 along headband path "H". The headband 302 is deflected from the plane of the flat-folded face mask 300 adjacent to exhalation valve 308. To apply the face mask 300, the user turns the face mask 300 inside out with respect to the two-part headband 302. When the headband is opposite the rear of the mask 300, the attachment locations 304, 306 are in a peel configuration. FIG. 21 corresponds to the embodiment illustrated in FIG. 20 in all respects, except that a one-part headband 302a is attached to the face mask 300a.

Figure 22:
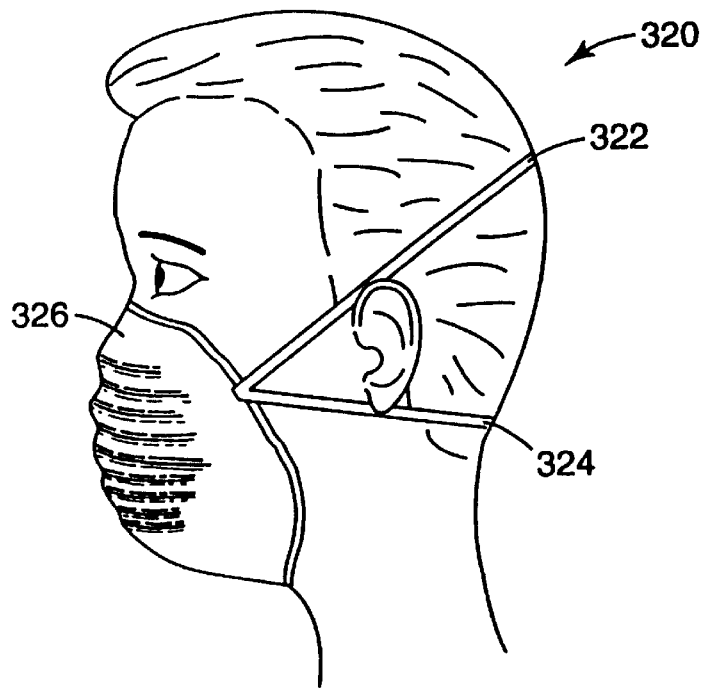
FIG. 22 illustrates the application of a two-part headband on an exemplary face mask.
Figure 23:
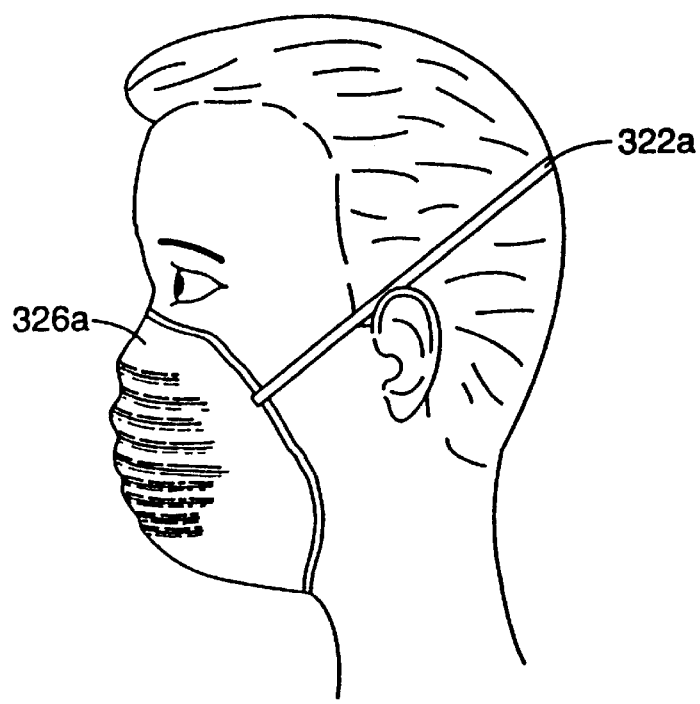
FIG. 23 illustrates a one-part headband attached to an exemplary face mask.

FIG. 22 illustrates the operation of a two-part headband 320 retaining an exemplary face mask 326 to a user. The two-part headband 320 includes a head strap 322 and a neck strap 324. It will be understood that a headband with three or more straps may be desirable for some applications. FIG. 23 illustrates a one-part headband 322a retaining an exemplary face mask 326a to a user.

Figure 24:
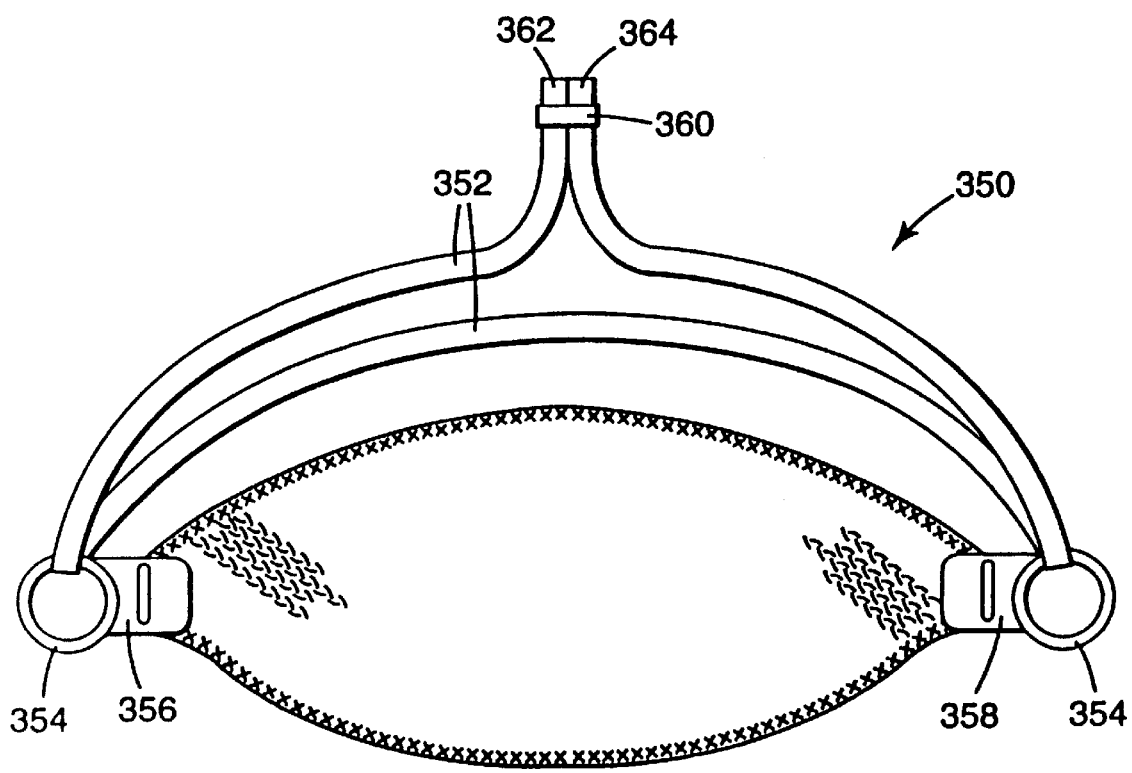
FIG. 24 illustrates a continuous loop headband entrapped by the face mask blank.

FIG. 24 is an alternate flat-folded respirator mask 350 shown from the front in its folded, storage configuration for use with a continuous loop headband 352. The ends 362, 364 of the headband 352 are joined by a sliding clamp 360. Attachment rings 354 are connected to the left and right attachment locations 356, 358 for entrapping the loop headband 352. It will be understood that a variety of attachment configurations may be substituted for the attachment rings 354, such as openings or slots in the face mask blank.

Filter Media

The filter media or material useful in the present invention includes a number of woven and nonwoven materials, a single or a plurality of layers, with or without an inner or outer cover or scrim, and with or without a stiffening means. In the embodiment illustrated in FIG. 4A–4D, the central portion is provided with stiffening member. Examples of suitable filter material include microfiber webs, fibrillated film webs, woven or nonwoven webs (e.g., airlaid or carded staple fibers), solution-blown fiber webs, or combinations thereof. Fibers useful for forming such webs include, for example, polyolefins such as polypropylene, polyethylene, polybutylene, poly(4-methyl-1-pentene) and blends thereof, halogen substituted polyolefins such as those containing one or more chloroethylene units, or tetrafluoroethylene units, and which may also contain acrylonitrile units, polyesters, polycarbonates, polyurethanes, rosin-wool, glass, cellulose or combinations thereof.

Fibers of the filtering layer are selected depending upon the type of particulate to be filtered. Proper selection of fibers can also affect the comfort of the respirator to the wearer, e.g., by providing softness or moisture control. Webs of melt blown microfibers useful in the present invention can be prepared as described, for example, in Wente, Van A., "Superfine Thermoplastic Fibers" in *Industrial Engineering Chemistry*, Vol. 48, 1342 et seq. (1956) and in Report No. 4364 of the Naval Research Laboratories, published May 25, 1954, entitled "Manufacture of Super Fine Organic Fibers" by Van A. Wente et al. The blown microfibers in the filter media useful on the present invention preferably have an effective fiber diameter of from 3 to 30 micrometers, more preferably from about 7 to 15 micrometers, as calculated according to the method set forth in Davies, C. N., "The Separation of Airborne Dust Particles", Institution of Mechanical Engineers, London, Proceedings 1B, 1952.

Staple fibers may also, optionally, be present in the filtering layer. The presence of crimped, bulking staple fibers provides for a more lofty, less dense web than a web consisting solely of blown microfibers. Preferably, no more than 90 weight percent staple fibers, more preferably no more than 70 weight percent are present in the media. Such webs containing staple fiber are disclosed in U.S. Pat. No. 4,118,531 (Hauser), which is incorporated herein by reference.

Bicomponent staple fibers may also be used in the filtering layer or in one or more other layers of the filter media. The bicomponent staple fibers which generally have an outer layer which has a lower melting point than the core portion can be used to form a resilient shaping layer bonded together at fiber intersection points, e.g., by heating the layer so that the outer layer of the bicomponent fibers flows into contact with adjacent fibers that are either bicomponent or other staple fibers. The shaping layer can also be prepared with binder fibers of a heat-flowable polyester included together with staple fibers and upon heating of the shaping layer the binder fibers melt and flow to a fiber intersection point where they surround the fiber intersection point. Upon cooling, bonds develop at the intersection points of the fibers and hold the fiber mass in the desired shape. Also, binder materials such as acrylic latex or powdered heat activatable adhesive resins can be applied to the webs to provide bonding of the fibers.

Fibers subject to an electrical charge such as are disclosed in U.S. Pat. No. 4,215,682 (Kubik et al.), U.S. Pat. No. 4,588,537 (Klasse et al.), polarizing or charging electrets as disclosed in U.S. Pat. No. 4,375,718 (Wadsworth et al.), or U.S. Pat. No. 4,592,815 (Nakao), or electrically charged fibrillated-film fibers as disclosed in U.S. Pat. No. RE. 31,285 (van Turnhout), which are hereby incorporated herein by reference, are useful in the present invention. In general the charging process involves subjecting the material to corona discharge or pulsed high voltage.

Sorbent particulate material such as activated carbon or alumina may also be included in the filtering layer. Such particle-loaded webs are described, for example, in U.S. Pat. No. 3,971,373 (Braun), U.S. Pat. No. 4,100,324 (Anderson) and U.S. Pat. No. 4,429,001 (Kolpin et al.), which are incorporated herein by reference. Masks from particle loaded filter layers are particularly good for protection from gaseous materials.

At least a portion of the face masks include a filter media. In the embodiment illustrated in FIGS. 7 and 8, at least two of the upper, central and lower portions comprise filter media and all of the upper, central and lower portions may comprise filter media. The portion(s) not formed of filter media may be formed of a variety of materials. The upper portion may be formed, for example, from a material which provides a moisture barrier to prevent fogging of a wearer's glasses, or of a transparent material which could extend upward to form a face shield. The central portion may be formed of a transparent material so that lip movement by the wearer can be observed.

Where the central portion is bonded to the upper and/or lower portions, bonding can be carried out by ultrasonic welding, adhesives, glue, hot melt adhesives, staple, sewing, thermomechanical, pressure, or other suitable means and can be intermittent or continuous. Any of these means leaves the bonded area somewhat strengthened or rigidified.

A nose clip useful in the respirator of the present invention may be made of, for example, a pliable dead-soft band of metal such as aluminum or plastic coated wire and can be shaped to fit the mask comfortably to a wearere's face. Particularly preferred is a non-linear nose clip configured to extend over the bridge of the wearer's nose having inflections disposed along the clip section to afford wings that assist in providing a snug fit of the mask in the nose and cheek area. The nose clip may be secured to the mask by an adhesive, for example, a pressure sensitive adhesive or a liquid hot-melt adhesive. Alternatively, the nose clip may be encased in the body of the mask or it may be held between the mask body and a fabric or foam that is mechanically or adhesively attached thereto. In a preferred embodiment of the invention, the nose clip is positioned on the outside part of the upper portion and a foam piece is disposed on the inside part of the upper portion of the respirator in alignment with the nose clip.

The respirator may also include an optional exhalation valve, typically a diaphragm valve, which allows for the easy exhalation of air by the user. An exhalation valve having extraordinary low pressure drop during exhalation for the mask is described in U.S. Pat. No. 5,325,892 (Japuntich et al.) which is incorporated herein by reference. Many exhalation valves of other designs are well known to those skilled in the art. The exhalation valve is preferably secured to the respirator central portion, preferably near the middle of the central portion, by sonic welds, adhesion bonding, and particularly mechanical clamping or the like.

EXAMPLES

Headbands made according to the method of the present invention are further described by way of the non-limiting examples set forth below:

In examples 1–3 elastomeric composites with microtextured skin layers were prepared as described in U.S. patent application Ser. No. 07/503716, filed Mar. 30, 1990, and used to make headbands. In all cases the headband width was 10 mm prior to activation. The force data corresponds to an average of the force measured during the outgoing elongation cycle and the return cycle.

A range of user head sizes was determined from the information on test panel subjects described by S. G. Danisch, H. E. Mullins, and C. R. Rhoe, Appl. Occup. Environ. Hyg., 7(4), 241–245 (1992), which is based on recommendations from the Los Alamos National Laboratory. The facial characteristics of this panel appears to simulate the facial characteristics of 95% of the American workforce. Individuals were evaluated with regard to the anthropometric parameters of face length (menton-nasal root depression length) and face width (bizygomatic breadth) as described in the above paper. Three individuals were selected whose facial characteristics were small (108 mm length, 123 mm width), medium (120 mm length, 138 mm width), and large (136 mm length, 148 mm width) according to the distribution of facial sizes described in the above paper. It was assumed that these small, medium, and large facial sizes also correspond to small, medium, and large head sizes.

Headbands were cut to a length of 220 mm, laid flat on a flat folded respirator that was 220 mm long, and attached at both ends by stapling. The stretchable length was 200 mm. The mask was then placed on each of the test subjects and the elongation of the headband was measured at its maximum length on the back of the head and at its minimum length on the back of the neck. The results are given in Table 1.

TABLE I

Percent Headband Elongation for Various Head Sizes

|  | Small | Medium | Large |
|---|---|---|---|
| Head | 106% | 136% | 165% |
| Neck | 30% | 58% | 95% |

Headband materials of this invention were cut to a length of 220 mm and activated by stretching to 300%–400% of their original length and releasing. The elongation of these materials were determined for various stretching forces, a plot of the relationship between the force and elongation was determined, and the force of attachment for each of the preselected representative head and neck sizes was determined.

Example 1 and Comparative Example C1

An elastomeric composite was prepared as described in U.S. patent application Ser. No. 07/503716 filed Mar. 30, 1990. The core material was Kraton™G 1657, a (styrene-ethylene butylene-styrene) block copolymer (Shell Chemical Company, Beaupre, Ohio). Two skin layers, one on each side, were made of polypropylene PP 3445 (Exxon Chemical Company, Houston, Tex.). The ratio of the thickness of the core layer to each skin layer was 19 to 1. The thickness of the composite was 6 mils (0.15 millimeters). The following forces of attachment were determined.

Forces of Attachment in Grams
Kraton ™ G 1657 and Polypropylene PP 3445

|  | Small | Medium | Large |
|---|---|---|---|
| Head | 160 | 190 | 210 |
| Neck | 70 | 115 | 155 |

For comparison, a polyurethane elastomeric headband from a commercially available respirator (Model DMR2010, Technol Medical Products, Inc., Fort Worth, Tex.) with a width of 6 mm and a length of 220 mm was similarly evaluated with the following results.

Comparative Example C1
Forces of Attachment in Grams
Polyurethane Headband

|  | Small | Medium | Large |
|---|---|---|---|
| Head | 240 | 280 | 315 |
| Neck | 80 | 150 | 220 |

It can be seen that the headband of this invention provides a relatively constant force of attachment over a range of head sizes in comparison with current commercially available headbands, and that it provides adequate forces of attachment for smaller head sizes while not causing uncomfortably large forces for wearers with larger head sizes.

Example 2

In this example different elastomeric materials were used in the headbands of this invention. In one case the elastomer was Kraton™D 1107, a styrene-isoprene-styrene block copolymer, with 0.5% Irganox 1010 (Ciba Geigy Corp., Hawthorne, N.Y.) added as a stabilizer. In another case the elastomer was Kraton ™G 1657, a (styrene-ethylene butylene-styrene) block copolymer, with 5% Engage™8200 (Dow Chemical Company, Midland, Mich.) added as a processing aid. The skin layers were PP 7C50 polypropylene (Shell Chemical Company, Beaupre, Ohio.). The ratio of the thickness of the core layer to one skin layer was 38 to 1. The thickness of the composite was 8 mils (0.20 millimeters). The results are given below.

Forces of Attachment in Grams
Different Elastomers

|  | Kraton ™ D 1107 | Kraton ™ G 1657 |
|---|---|---|
| Head - Small | 105 | 220 |
| Head - Medium | 115 | 245 |
| Head - Large | 135 | 290 |
| Neck - Small | 45 | 120 |
| Neck - Medium | 75 | 170 |
| Neck - Large | 95 | 210 |

It can be seen that Kraton™G 1657, which is stiffer than Kraton™D 1107, provides a larger force of attachment than Kraton™D 1107 does, with other variables held constant.

Example 3

In this example different thicknesses of an elastomeric composite made with the same elastomer were used in the headbands of this invention. The elastomer was Kraton™D 1107 with 0.5% Irganox™1010 and 0.5% Irganox™1076 (Ciba- Geigy Corp., Hawthorne, N.Y.) added as stabilizers. The skin layers were PP 3445 polypropylene (Exxon Chemical Company, Houston, Tex.). The ratio of the thickness of the core layer to one skin layer was 18.5 to 1. The results are given below.

| Thickness | Force of Attachment in Grams Different Thicknesses | | |
|---|---|---|---|
| | 8.1 mils (0.21 mm) | 10.9 mils (0.28 mm) | 11.7 mils (0.30 mm) |
| Head - Small | 75 | 125 | 140 |
| Head - Medium | 90 | 150 | 175 |
| Head - Large | 130 | 350 | 450 |
| Neck - Small | 40 | 60 | 70 |
| Neck - Medium | 60 | 90 | 105 |
| Neck - Large | 75 | 120 | 125 |

It can be seen that the force of attachment for a given elastomer can be tailored by selecting the thickness of the composite headband material.

Example 4

Flat-folded Face Masks

Flat-folded face masks made generally according to the method of FIGS. 4A–4D are further described by way of the non-limiting examples set forth below.

Two sheets (350 mm×300 mm) of electrically charged melt blown polypropylene microfibers were placed one atop the other to form a layered web having a basis weight of 100 g/m², an effective fiber diameter of 7 to 8 microns, and a thickness of about 1 mm. An outer cover layer of a light spunbond polypropylene web (350 mm×300 mm; 50 g/m², Type 105OBIUO0, available from Don and Low Nonwovens, Forfar, Scotland, United Kingdom) was placed in contact with one face of the microfiber layered web. A strip of polypropylene support mesh (380 mm×78 mm; 145 g/m², Type 5173, available from Intermas, Barcelona, Spain) was placed widthwise on the remaining microfiber surface approximately 108 mm from one long edge of the layered microfiber web and 114 mm from the other long edge of the layered microfiber web and extending over the edges of the microfiber surface. An inner cover sheet (350 mm×300 mm; 23 g/m², LURTASIL™6123, available from Spun Web UK, Derby, England, United Kingdom) was placed atop the support mesh and the remaining exposed microfiber web. The five-layered construction was then ultrasonically bonded in a rectangular shape roughly approximating the layered construction to provide bonds which held the layered construction together at its perimeter forming a top edge, a bottom edge and two side edges. The layers were also bonded together along the long edges of the support mesh. The length of the thus-bonded construction, measured parallel to the top and bottom edges, was 188 mm; and the width, measured parallel to the side edges was 203 mm. The edges of the strip of support mesh lay 60 mm from the top edge of the layered construction and 65 mm from the bottom edge of the construction. Excess material beyond the periphery of the bond was removed, leaving portions beyond the bond line at the side edges, proximate the centerline of the support mesh, 50 mm long×20 mm wide to form headband attachment means.

The top edge of the layered construction was folded lengthwise proximate the nearest edge of the support mesh to form an upper fold such that the inner cover contacted itself for a distance of 39 mm from the upper fold to form an upper portion, the remaining 21 mm of layered construction forming an additional top portion. The bottom edge of the layered construction was folded lengthwise proximate the nearest edge of the support mesh to form a lower fold such that the inner cover contacted itself for a distance of 39 mm to form a lower portion, the remaining 26 mm forming the additional lower portion. The inner cover layer of the additional upper portion and the additional lower portion were then in contact with each other. The contacting portions of the central portion, lying between the upper and lower folds, the upper portion and the lower portion were sealed at their side edges.

A malleable nose clip about 5 mm wide×140 mm long was attached to the exterior surface of the additional upper portion and a strip of nose foam about 15 mm wide×140 mm long was attached to the inner surface of the additional upper portion substantially aligned with the nose clip. The additional upper and lower portions were folded such that the outer covers of each contacted the outer cover of the upper and lower potions, respectively.

The free ends of the layered construction left to form headband attachment means were folded to the bonded edge of the layered construction and bonded to form loops. Headband elastic was threaded through the loops to provide means for securing the thus-formed respirator to a wearer's face.

Example 5

First and second layered sheet constructions (350 mm×300 mm) were prepared as in Example 4 except the support mesh was omitted. A curvilinear bond was formed along a long edge of each sheet and excess material beyond the convex portion of the bond was removed. A third layered sheet construction was prepared as in Example 4 except each of the five layers was substantially coextensive. The first layered sheet construction was placed atop the third layered sheet construction with inner covers in contact. The first and third sheet constructions were bonded together using a curvilinear bond near the unbonded long edged of the first sheet construction to form an elliptical upper respirator portion having a width of 165 mm and a depth of 32 mm. The radius of each of the curvilinear bond was 145 mm.

The edge of the first sheet construction not bonded to the third sheet was folded back toward the edge of the first sheet which was bonded to the third sheet. The second sheet construction was placed atop the folded first sheet and partially covered third sheet. The second and third sheet construction were bonded together using a curvilinear bond to form an elliptical lower respirator portion from the second sheet having a width of 165 mm and a depth of 32 mm and an elliptical central respirator portion having a width of 165 mm and a height of 64 mm from the third sheet construction. The material outside the elliptical portions was removed. The upper and lower portions were folded away from the central portion.

A malleable aluminum nose clip was attached to the exterior surface of the periphery of the upper portion and a strip of nose foam was attached to the interior surface in substantial alignment with the nose clip. Headband attachment means were attached at the points where the bonds between the central portion and the upper and lower portions met, and headband elastic was threaded through the attachment means to form a respirator ready for a wearer to don.

The various modifications and alterations of this invention will be apparent to those skilled in the art without departing from the scope and spirit of this invention and this invention should not be restricted to that set forth herein for illustrative purposes.

What is claimed is:

1. A process for attaching a multi-part headband to a face mask, comprising the steps of:

preparing a face mask blank having left and right headband attachment locations, the face mask blank having a headband path extending between the left and right headband attachment locations;

positioning a headband material along the headband path;

attaching the headband material to at least one of the left and right headband attachment locations; and forming at least one longitudinal score line in the headband material, whereby the at least one longitudinal score line defines at least a two-part headband.

2. The process of claim 1 wherein the step of forming the at least one longitudinal score line occurs prior to the step of attaching the headband material to at least one of the left and right attachment locations.

3. The process of claim 1 wherein the headband material comprises at least one continuous thermoplastic skin layer secured to at least one elastomeric core, the headband material having a first modulus in an unactivated state and a second, lower modulus in an activated state, the thermoplastic skin layer forming a microtextured permanently deformed skin layer when the headband material is in the activated state.

4. The process of claim 3 wherein the elastomeric core and the at least one thermoplastic layer are in continuous contact in the activated state.

5. The process of claim 3 further including the step of stretch activating at least a portion of the headband material subsequent to the step of attaching the headband material.

6. The process of claim 3 further including the step of stretch activating at least a portion of the headband material prior to the step of attaching the headband material.

7. The process of claim 3 wherein the unactivated state is visually distinguishable from the activated state to provide an indication of tampering.

8. The process of claim 1 wherein the headband path comprises an axis intersecting the left and right headband attachment locations.

9. The process of claim 1 wherein the headband path generally follows a contour of a surface of the face mask blank.

10. The process of claim 1 wherein the at least one longitudinal score line in the headband material comprises at least one slit.

11. The process of claim 1 wherein the at least one longitudinal score line terminates prior to the left and right headband attachment locations.

12. The process of claim 1 further including the step of forming at least one punch-out in the headband material proximate an end of the at least one longitudinal score line.

13. The process of claim 1 further including the step of forming a first lateral score line extending from a first end of the at least one longitudinal score line to an edge of the headband material and a second lateral score line extending from a second end of the at least one longitudinal score line to an opposite edge of the headband material.

14. The process of claim 1 further including the step of separating the headband material along the at least one longitudinal score line to form a two-part headband.

15. The process of claim 1 wherein the at least one longitudinal score line comprises a pair of ear receiving slits formed in the headband material proximate the left and right attachment locations, the process further including the steps of forming a score line in the headband material orthogonal to the headband path proximate a midpoint between the left and right headband attachment points to form left and right headband portions.

16. The process of claim 1 wherein the at least one longitudinal score line is off-center.

17. The process of claim 1 wherein the face mask blank comprises a molded cup-shaped respirator mask blank.

18. The process of claim 1 wherein the face mask blank comprises a flat-folded respirator mask blank.

19. The process of claim 1 wherein the face mask blank comprises a surgical mask.

20. The process of claim 1 wherein the method of attaching the headband material to the face mask blank is selected from a group consisting of thermal bonding, ultrasonic welding, adhesives, pressure sensitive adhesives, glues, staples and fasteners.

21. The process of claim 1 wherein the step of preparing the face mask blank comprises the step of bonding portions of the face mask blank to form the face mask generally simultaneously with the step of attaching the headband material.

22. The process of claim 1 wherein the step of preparing the face mask blank comprises the step of configuring at least one web of face mask blank material to interpose the left and right attachment locations therebetween.

23. The process of claim 1 wherein the left and right attachment locations are located on an external surface of the face mask blank.

24. The process of claim 1 wherein the step of positioning a headband material comprises feeding the headband material from a continuous roll of headband material.

25. The process of claim 1 wherein the step of preparing a face mask blank comprises arranging at least one web into a face mask blank, at least a portion of the at least one web comprising a filter media.

26. The process of claim 1 wherein the step of preparing a face mask blank comprises the steps of:

forming a flat central portion of sufficient width to extend across a wearer's face from about cheekbone to cheekbone over the nose area, said central portion having at least an upper edge and a lower edge;

attaching a flat upper portion substantially coextensively with the upper edge of the central portion; and attaching a flat lower portion substantially coextensively with the lower edge of the central portion.

27. The process of claim 26 wherein the flat central portion, upper portion and lower portion comprise a generally elliptical shape.

28. The process of claim 1 wherein the step of preparing a face mask blank comprises forming a plurality of fabric webs into a face mask blank.

29. The process of claim 1 wherein at least a portion of the face mask blank comprises melt blown microfibers.

30. The process of claim 1 further including the step of installing an exhalation valve on the face mask blank.

31. A face mask preparable by the process of claim 1.

* * * * *